(12) United States Patent
Rustad et al.

(10) Patent No.: US 9,724,490 B2
(45) Date of Patent: Aug. 8, 2017

(54) CAPILLARY HEATER WIRE

(71) Applicant: CareFusion 207, Inc., San Diego, CA (US)

(72) Inventors: Andre M. Rustad, Etiwanda, CA (US); Neil Alex Korneff, Diamond Bar, CA (US)

(73) Assignee: CAREFUSION 207, INC., San Diego, CA (US)

( * ) Notice: Subject to any disclaimer, the term of this patent is extended or adjusted under 35 U.S.C. 154(b) by 0 days.

(21) Appl. No.: 14/971,953

(22) Filed: Dec. 16, 2015

(65) Prior Publication Data

US 2016/0101258 A1  Apr. 14, 2016

Related U.S. Application Data

(63) Continuation of application No. 13/539,234, filed on Jun. 29, 2012, now Pat. No. 9,242,064, which is a (Continued)

(51) Int. Cl.
*A61M 16/10* (2006.01)
*A61M 16/08* (2006.01)
(Continued)

(52) U.S. Cl.
CPC .... *A61M 16/1095* (2014.02); *A61M 16/0875* (2013.01); *A61M 16/0883* (2014.02); *A61M 16/109* (2014.02); *A61M 16/142* (2014.02); *A61M 16/16* (2013.01); *A61M 16/162* (2013.01); *A61M 16/164* (2014.02); *H05B 1/025* (2013.01); *H05B 3/54* (2013.01);
(Continued)

(58) Field of Classification Search
CPC .......... A61M 16/0883; A61M 16/0891; A61M 16/0975; A61M 16/1095; A61M 16/108; A61M 16/1085; A61M 16/0875
See application file for complete search history.

(56) References Cited

U.S. PATENT DOCUMENTS

| 1,144,508 A | 6/1915 | Taylor, Jr. |
| 2,256,991 A | 9/1941 | Sabins |
| (Continued) | | |

FOREIGN PATENT DOCUMENTS

| DE | 10016005 A1 | 12/2001 |
| EP | 0391814 A2 | 10/1990 |
| (Continued) | | |

OTHER PUBLICATIONS

Extended European Search Report for European Application No. 13769160.6, dated Jan. 7, 2016, 15 pages.
(Continued)

*Primary Examiner* — Valerie L Woodward
(74) *Attorney, Agent, or Firm* — McDermott Will & Emery LLP

(57) ABSTRACT

A heater wire including at least one extending component disposed thereon. The heater wire is positioned within a respiratory gas conduit. The heater wire may include a wire component and a groove that extends along a length of the heater wire. The heater wire may also include threads extending from an outer surface of the heater wire that faces away from the wire component. The threads may be woven or braided threads.

19 Claims, 28 Drawing Sheets

Related U.S. Application Data continuation-in-part of application No. 13/250,894, filed on Sep. 30, 2011, now Pat. No. 9,205,220.

(51) Int. Cl.
| | |
|---|---|
| *A61M 16/16* | (2006.01) |
| *H05B 1/02* | (2006.01) |
| *A61M 16/14* | (2006.01) |
| *H05B 3/54* | (2006.01) |
| *H05B 6/80* | (2006.01) |
| *A61M 16/00* | (2006.01) |
| *A61M 16/06* | (2006.01) |

(52) U.S. Cl.
CPC ......... *H05B 6/804* (2013.01); *A61M 16/0051* (2013.01); *A61M 16/0066* (2013.01); *A61M 16/0683* (2013.01); *A61M 2016/0039* (2013.01); *A61M 2205/14* (2013.01); *A61M 2205/3306* (2013.01); *A61M 2205/3389* (2013.01); *A61M 2205/368* (2013.01); *A61M 2205/502* (2013.01); *A61M 2205/6009* (2013.01); *A61M 2205/6018* (2013.01); *A61M 2205/6054* (2013.01); *A61M 2205/6072* (2013.01); *A61M 2205/6081* (2013.01); *H05B 2203/014* (2013.01); *H05B 2203/021* (2013.01); *H05B 2203/022* (2013.01); *H05B 2203/032* (2013.01); *Y10T 29/49083* (2015.01); *Y10T 29/49826* (2015.01)

(56) References Cited

U.S. PATENT DOCUMENTS

| | | | |
|---|---|---|---|
| 3,811,496 A * | 5/1974 | Asselman | F28D 15/046 |
| | | | 165/104.26 |
| 3,893,458 A | 7/1975 | Fletcher et al. | |
| 4,013,742 A | 3/1977 | Lang | |
| 4,098,853 A | 7/1978 | Brown et al. | |
| 4,216,176 A | 8/1980 | Tanaka | |
| 4,303,601 A | 12/1981 | Grimm et al. | |
| 4,354,984 A | 10/1982 | Richardson et al. | |
| 4,386,582 A | 6/1983 | Adsit | |
| 4,441,027 A | 4/1984 | Richardson et al. | |
| 4,477,494 A | 10/1984 | Ali-Zaidi | |
| 4,630,475 A | 12/1986 | Mizoguchi | |
| 4,644,790 A | 2/1987 | Mizoguchi | |
| 4,682,010 A | 7/1987 | Drapeau et al. | |
| 4,921,642 A | 5/1990 | LaTorraca | |
| 5,052,476 A | 10/1991 | Sukumoda et al. | |
| 5,195,515 A | 3/1993 | Levine | |
| 5,231,979 A | 8/1993 | Rose et al. | |
| 5,286,942 A | 2/1994 | McFadden et al. | |
| 5,373,841 A | 12/1994 | Kyllonen et al. | |
| 5,383,574 A | 1/1995 | Raphael | |
| 5,438,233 A | 8/1995 | Boland et al. | |
| 5,577,494 A | 11/1996 | Kuypers et al. | |
| 5,586,214 A | 12/1996 | Eckman | |
| 5,640,951 A | 6/1997 | Huddart et al. | |
| 6,167,883 B1 * | 1/2001 | Beran | A61M 16/1075 |
| | | | 128/203.17 |
| 6,246,045 B1 | 6/2001 | Morris et al. | |
| 6,272,933 B1 | 8/2001 | Gradon et al. | |
| 6,335,517 B1 | 1/2002 | Chauviaux et al. | |
| 6,349,722 B1 | 2/2002 | Gradon et al. | |
| 6,584,972 B2 | 7/2003 | McPhee | |
| 6,694,974 B1 | 2/2004 | George-Gradon et al. | |
| 6,766,817 B2 | 7/2004 | da Silva | |
| 6,802,314 B2 | 10/2004 | McPhee | |
| 6,804,656 B1 | 10/2004 | Rosenfeld et al. | |
| 6,918,389 B2 | 7/2005 | Seakins et al. | |
| 7,043,979 B2 | 5/2006 | Smith et al. | |
| 7,051,733 B2 | 5/2006 | Gradon et al. | |
| 7,207,945 B2 | 4/2007 | Bardy | |
| 7,263,994 B2 | 9/2007 | Gradon et al. | |
| 7,559,324 B2 | 7/2009 | Smith et al. | |
| 7,637,287 B2 * | 12/2009 | Reinhard | F16L 35/00 |
| | | | 138/108 |
| 7,651,542 B2 | 1/2010 | Shurtleff et al. | |
| 7,959,574 B2 | 6/2011 | Bardy | |
| 8,037,882 B2 * | 10/2011 | Smith | A61M 16/08 |
| | | | 128/200.18 |
| 8,578,789 B2 | 11/2013 | Murata | |
| 8,733,348 B2 | 5/2014 | Korneff et al. | |
| 9,205,220 B2 | 12/2015 | Korneff et al. | |
| 2002/0078958 A1 | 6/2002 | Stenzler | |
| 2004/0016430 A1 | 1/2004 | Makinson et al. | |
| 2004/0221844 A1 | 11/2004 | Hunt et al. | |
| 2005/0139211 A1 | 6/2005 | Alston et al. | |
| 2006/0124127 A1 | 6/2006 | Du et al. | |
| 2006/0278222 A1 | 12/2006 | Schermeier et al. | |
| 2007/0107801 A1 | 5/2007 | Cochran et al. | |
| 2007/0144519 A1 | 6/2007 | Henry et al. | |
| 2008/0035154 A1 | 2/2008 | Johnson | |
| 2008/0066751 A1 | 3/2008 | Polacsek | |
| 2008/0072904 A1 | 3/2008 | Becker et al. | |
| 2008/0078386 A1 | 4/2008 | Feldhahn et al. | |
| 2008/0190427 A1 | 8/2008 | Payton et al. | |
| 2008/0308100 A1 | 12/2008 | Pujol et al. | |
| 2009/0000620 A1 | 1/2009 | Virr | |
| 2009/0025723 A1 * | 1/2009 | Schobel | A61M 16/0666 |
| | | | 128/204.17 |
| 2009/0159079 A1 | 6/2009 | Meier | |
| 2009/0173344 A1 | 7/2009 | Short | |
| 2009/0301482 A1 | 12/2009 | Burton et al. | |
| 2010/0044267 A1 | 2/2010 | Tolibas-Spurlock et al. | |
| 2010/0083965 A1 | 4/2010 | Virr et al. | |
| 2010/0132708 A1 | 6/2010 | Martin et al. | |
| 2010/0230503 A1 | 9/2010 | Nakaguro | |
| 2011/0023874 A1 | 2/2011 | Bath et al. | |
| 2011/0120462 A1 | 5/2011 | Tatkov et al. | |
| 2011/0253136 A1 | 10/2011 | Sweeney et al. | |
| 2011/0265024 A1 | 10/2011 | Leone et al. | |
| 2012/0167880 A1 | 7/2012 | Jacob | |
| 2012/0227738 A1 | 9/2012 | Virr et al. | |
| 2013/0081582 A1 | 4/2013 | Varga | |
| 2013/0081618 A1 | 4/2013 | Korneff et al. | |
| 2013/0081620 A1 | 4/2013 | Korneff et al. | |
| 2013/0081621 A1 | 4/2013 | Korneff et al. | |
| 2013/0081622 A1 | 4/2013 | Korneff et al. | |
| 2013/0081625 A1 | 4/2013 | Rustad et al. | |
| 2013/0081701 A1 | 4/2013 | Korneff et al. | |
| 2013/0255672 A1 | 10/2013 | Varga et al. | |
| 2014/0251331 A1 | 9/2014 | Korneff et al. | |

FOREIGN PATENT DOCUMENTS

| | | |
|---|---|---|
| EP | 0588214 A2 | 3/1994 |
| EP | 1671668 A1 | 6/2006 |
| EP | 2233167 A1 | 9/2010 |
| JP | H07219650 | 8/1995 |
| JP | H05285200 | 9/2013 |
| WO | WO-9718001 A1 | 5/1997 |
| WO | WO-03055553 | 7/2003 |
| WO | WO-2004105848 A1 | 12/2004 |
| WO | WO-2008095245 A1 | 8/2008 |
| WO | WO-2011058371 A1 | 5/2011 |

OTHER PUBLICATIONS

European Office Action for European Application No. 12835170, dated Mar. 20, 2015, 4 pages.
European Partial Supplementary Search Report for Application No. 13769160.6, dated Sep. 7, 2015, 8 pages.
Extended European Search Report for European Application No. 12835170, dated Mar. 3, 2015, 3 pages.
International Preliminary Report on Patentability for International Application No. PCT/US2012/058043, dated Apr. 1, 2014, 8pages.
International Preliminary Report on Patentability in PCT Application No. PCT/US2013/033946 dated Oct. 1, 2014.

(56) References Cited

OTHER PUBLICATIONS

International Search Report and Written Opinion for Interntaionl Application No. PCT/US2012/058043, dated Mar. 25, 2013, 13 pages.
International Search Report in PCT Application No. PCT/US2013/033946 dated Oct. 3, 2013.
Written Opinion of the International Searching Authority in PCT Application No. PCT/US2013/033946 dated Jul. 18, 2013.
European Office Action for Application No. 12835170.7, dated Mar. 27, 2017, 5 pages.

* cited by examiner

500

```
┌─────────────────────────────────────────────┐
│ SENSES, BY AT LEAST ONE SENSOR, WATER RELATED│
│ INFORMATION IN THE HUMIDIFICATION COMPONENT, │
│ THE AT LEAST ONE SENSOR POSITIONED EXTERNAL  │
│ TO THE HUMIDIFICATION COMPONENT AND COUPLED  │
│ WITH A CONTROL MODULE                        │
│ 502                                          │
└─────────────────────────────────────────────┘
```

SENSES, BY AT LEAST ONE SENSOR, WATER RELATED INFORMATION IN THE HUMIDIFICATION COMPONENT, THE AT LEAST ONE SENSOR POSITIONED EXTERNAL TO THE HUMIDIFICATION COMPONENT AND COUPLED WITH A CONTROL MODULE
502

↓

PROVIDES, BY THE AT LEAST ONE SENSOR, THE WATER RELATED INFORMATION INCLUDING DATA CONFIGURED FOR BEING USED TO CONTROL AN OPERATION OF A WATER LEVEL CONTROL ELEMENT
504

↓

BASED ON THE WATER RELATED INFORMATION, MAINTAINS A TARGET WATER LEVEL IN THE HUMIDIFICATION COMPONENT
506

↓

BASED ON THE WATER RELATED INFORMATION, COMPUTING AN OUTPUT OF A HUMIDIFICATION SYSTEM AND A QUANTITY OF WATER CONSUMED BY THE HUMIDIFICATION SYSTEM, WHEREIN THE HUMIDIFICATION SYSTEM INCLUDES THE HUMIDIFICATION COMPONENT
508

↓

BASED ON THE WATER RELATED INFORMATION, DETECTS A LACK OF WATER OR DETECTS AN EXCESS AMOUNT OF WATER IN THE HUMIDIFICATION SYSTEM, WHEREIN THE HUMIDIFICATION SYSTEM INCLUDES THE HUMIDIFICATION COMPONENT
510

```
┌─────────────────────────────────────────┐
│ PROVIDES A HUMIDIFICATION COMPONENT THAT HOLDS A │
│              WATER VOLUME                │
│                  602                     │
└─────────────────────────────────────────┘
                    │
                    ▼
┌─────────────────────────────────────────┐
│ COUPLES AT LEAST ONE SENSOR WITH A CONTROL MODULE, │
│   THE AT LEAST ONE SENSOR SENSES WATER RELATED │
│   INFORMATION IN THE HUMIDIFICATION COMPONENT AND │
│   PROVIDES THE WATER RELATED INFORMATION TO THE │
│    CONTROL MODULE, THE WATER RELATED INFORMATION │
│    INCLUDES DATA CONFIGURED FOR BEING USED BY THE │
│  CONTROL MODULE TO CONTROL AN OPERATION OF A WATER │
│   LEVEL CONTROL ELEMENT, WHEREIN THE AT LEAST ONE │
│   SENSOR IS POSITIONED EXTERNAL TO THE HUMIDIFICATION │
│                  COMPONENT               │
│                      604                 │
└─────────────────────────────────────────┘
```

```
┌─────────────────────────────────────────────────────────────┐
│ WICKS UP WATER FROM A REGION OF CONDENSATION WITHIN         │
│ A RESPIRATORY GAS CONDUIT, THE WICKING UP OF THE            │
│ WATER PERFORMED BY AT LEAST ONE GROOVE DISPOSED ON          │
│ A HEATER WIRE, THE HEATER WIRE BEING POSITIONED WITHIN      │
│ THE RESPIRATORY GAS CONDUIT                                 │
│ 1002                                                        │
└─────────────────────────────────────────────────────────────┘
                              │
                              ▼
┌─────────────────────────────────────────────────────────────┐
│ TRANSPORTS BY THE AT LEAST ONE GROOVE, WICKED UP            │
│ WATER FROM THE REGION OF CONDENSATION TO A                  │
│ RE-EVAPORATION REGION                                       │
│ 1004                                                        │
└─────────────────────────────────────────────────────────────┘
                              │
                              ▼
┌─────────────────────────────────────────────────────────────┐
│ EVAPORATES THE WICKED UP WATER BY A HOT SURFACE OF          │
│ THE HEATER WIRE                                             │
│ 1006                                                        │
└─────────────────────────────────────────────────────────────┘
```

```
RECEIVES, AT A HUMIDIFICATION CHAMBER, HEAT FROM A
HEAT SOURCE, THE HUMIDIFICATION CHAMBER CONFIGURED
FOR HOLDING A WATER VOLUME, WHEREIN THE
HUMIDIFICATION CHAMBER COMPRISES A NON-METALLIC
MATERIAL
1302
```

```
CONDUCTS, BY THE NON-METALLIC MATERIAL, RECEIVED HEAT
THROUGH THE HUMIDIFICATION CHAMBER INTO A WATER
VOLUME CONTAINED WITHIN THE HUMIDIFICATION CHAMBER
1304
```

WICK UP LIQUID FROM A REGION OF CONDENSATION WITHIN A RESPIRATORY GAS CONDUIT, THE WICKING UP LIQUID PERFORMED BY AT LEAST ONE EXTENDING COMPONENT DISPOSED ON A HEATER WIRE, WHEREIN THE HEATER WIRE IS POSITIONED WITHIN THE RESPIRATORY GAS CONDUIT
1905

TRANSPORT, BY THE AT LEAST ONE EXTENDING COMPONENT, WICKED UP LIQUID FROM A REGION OF CONDENSATION WITHIN THE RESPIRATORY GAS CONDUIT TO A RE-EVAPORATION REGION
1910

EVAPORATE THE WICKED UP LIQUID BY A HOT SURFACE OF THE HEATER WIRE
1915

PROVIDE A HEATER WIRE, THE HEATER WIRE CONFIGURED FOR HEATING GAS INSIDE AND BETWEEN AN INPUT AND OUTPUT END OF A RESPIRATORY GAS CONDUIT
2005

DISPOSE AT LEAST ONE EXTENDING COMPONENT ON THE HEATER WIRE
2010

CAPILLARY HEATER WIRE

CROSS REFERENCE TO RELATED APPLICATIONS

This Application is a continuation of U.S. patent application Ser. No. 13/539,234 entitled CAPILLARY HEATER WIRE, filed Jun. 29, 2012, which claims priority to and the benefit of and is a continuation in part of co-pending U.S. patent application Ser. No. 13/250,894, entitled FLUTED HEATER WIRE, filed Sep. 30, 2011, now issued as U.S. Pat. No. 9,205,220, which is related to: U.S. patent application Ser. No. 13/250,946 entitled HUMIDIFYING RESPIRATORY GASES, filed Sep. 30, 2011, now issued as U.S. Pat. No. 8,733,348; U.S. patent application Ser. No. 13/250,991 entitled MAINTAINING A WATER LEVEL IN A HUMIDIFICATION COMPONENT, filed Sep. 30, 2011, now issued as U.S. Pat. No. 9,212,673; U.S. patent application Ser. No. 13/251,030 entitled NON-METALLIC HUMIDIFICATION COMPONENT, filed Sep. 30, 2011; U.S. patent application Ser. No. 13/251,081 entitled HUMIDIFYING GAS FOR RESPIRATORY THERAPY, filed Sep. 30, 2011; and U.S. patent application Ser. No. 13/251,110 entitled REMOVING CONDENSATION FROM A BREATHING CIRCUIT, filed Sep. 30, 2011, now issued as U.S. Pat. No. 9,067,036.

This application is related to U.S. patent application Ser. No. 13/436,775 entitled TRANSPORTING LIQUID IN A RESPIRATORY COMPONENT, filed Mar. 30, 2012.

FIELD OF THE INVENTION

The present technology relates generally to the respiratory field. More particularly, the present technology relates to humidification.

BACKGROUND

Respiratory humidification systems are used in providing respiratory therapy to a patient. In general terms, the system includes a ventilator, humidifier and patient circuit. The ventilator supplies gases to a humidification chamber coupled with the humidifier. Water within the humidification chamber is heated by the humidifier, which produces water vapor that humidifies gases within the chamber. From the chamber, humidified gases are then carried to the patient through the patient circuit.

DESCRIPTION OF EMBODIMENTS

FIG. 5 is a flow diagram of an example method for maintaining a water level in a humidification component, in accordance with embodiments of the present technology.

FIG. 6 is a flow diagram of an example method for manufacturing a device for maintaining a water level in a humidification component, in accordance with embodiments of the present technology.

FIG. 10 is a flow diagram of an example method for automatically removing excess condensation from a breathing circuit, in accordance with embodiments of the present technology.

FIG. 13 shows a device for humidifying respiratory gases, in accordance with embodiments of the present technology.

FIG. 19 is a flow diagram of an example method for automatically removing excess condensation from a breathing circuit, in accordance with embodiments of the present technology.

DESCRIPTION OF EMBODIMENTS

Figure 1:
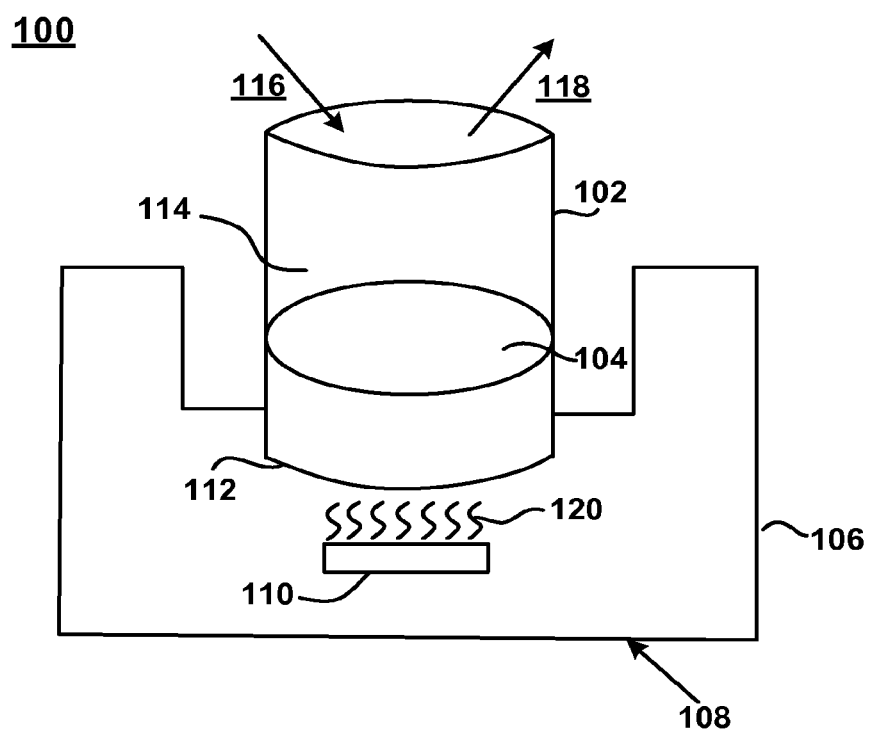
FIG. 1 shows a device for humidifying respiratory gases, in accordance with embodiments of the present technology.

Reference will now be made in detail to various embodiments, examples of which are illustrated in the accompanying drawings. While the subject matter will be described in conjunction with these embodiments, it will be understood that they are not intended to limit the subject matter to these embodiments. On the contrary, the subject matter described herein is intended to cover alternatives, modifications and equivalents, which may be included within the spirit and scope. Furthermore, in the following description, numerous specific details are set forth in order to provide a thorough understanding of the subject matter. However, some embodiments may be practiced without these specific details. In other instances, well-known structures and components have not been described in detail as not to unnecessarily obscure aspects of the subject matter.

Overview of Discussion

Herein, various embodiments of a humidification component and methods for providing respiratory therapy to a patient are described. The description begins with a brief general discussion of traditional humidification systems. This general discussion provides a framework of understanding for more particularized descriptions which follow in six separate sections. These six sections are dedicated and focused on a detailed discussion of particular features and concepts of operation associated with one or more embodiments of the described humidifier technology.

Humidification Systems

Traditional humidification systems for respiratory gas delivery in critical care and patient care settings typically involve a chamber of hot water which is used to provide vapor for humidifying the delivered gases. The method for heating this water bath is most often contact heating using a hot-plate or heating element which transfers heat to the water through a metallic surface which is incorporated into the humidification chamber. The metallic surface gets very hot and creates a danger of injury to those near the humidification system, since the hot-plate or heating element is accessible to a user.

The presence of this metallic element or base of the humidification chamber represents significant manufacturing and material costs in comparison to the other materials used in the humidification chamber such as polymers. It also necessitates a multi-step manufacturing process which involves attachment and water-tight sealing of this metallic section to a polymer section. This traditional method also necessitates a mechanism for providing good contact between the humidification chamber metallic surface and the heating element surface to ensure good conduction. Further, after each patient uses the humidification chamber, it is discarded, along with its expensive metallic base. A new humidification chamber must be manufactured, increasing the cost of using the humidification system.

Additionally, for customers to use the present-day humidification systems, they must obtain a water bag, connect a tube set to the bag and the humidification chamber, and then fill the humidification chamber with the water from the water bag.

Embodiments of the present technology provide a method and device for at least, but not limited to, humidifying respiratory gases, maintaining a water level in a humidification component, removing condensation from a humidification component and conducting heat utilizing a non-metallic humidification component. Of note, in one embodiment the humidification component described herein is a structure that retains a fluid therein for humidifying. However, in another embodiment, the humidification component described herein simply refers to the presence of moisture provided.

Figure 15A:
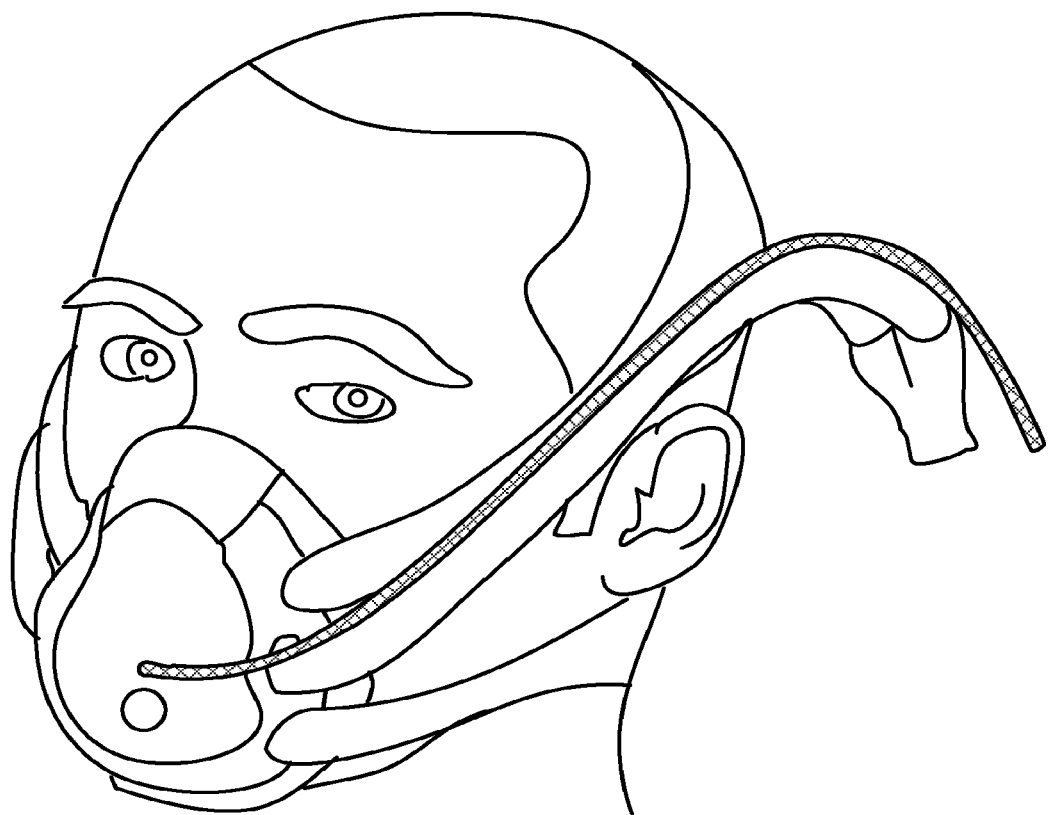
FIG. 15A shows a front perspective view of a patient breathing through a mask through the upper airways.
Figure 15B:
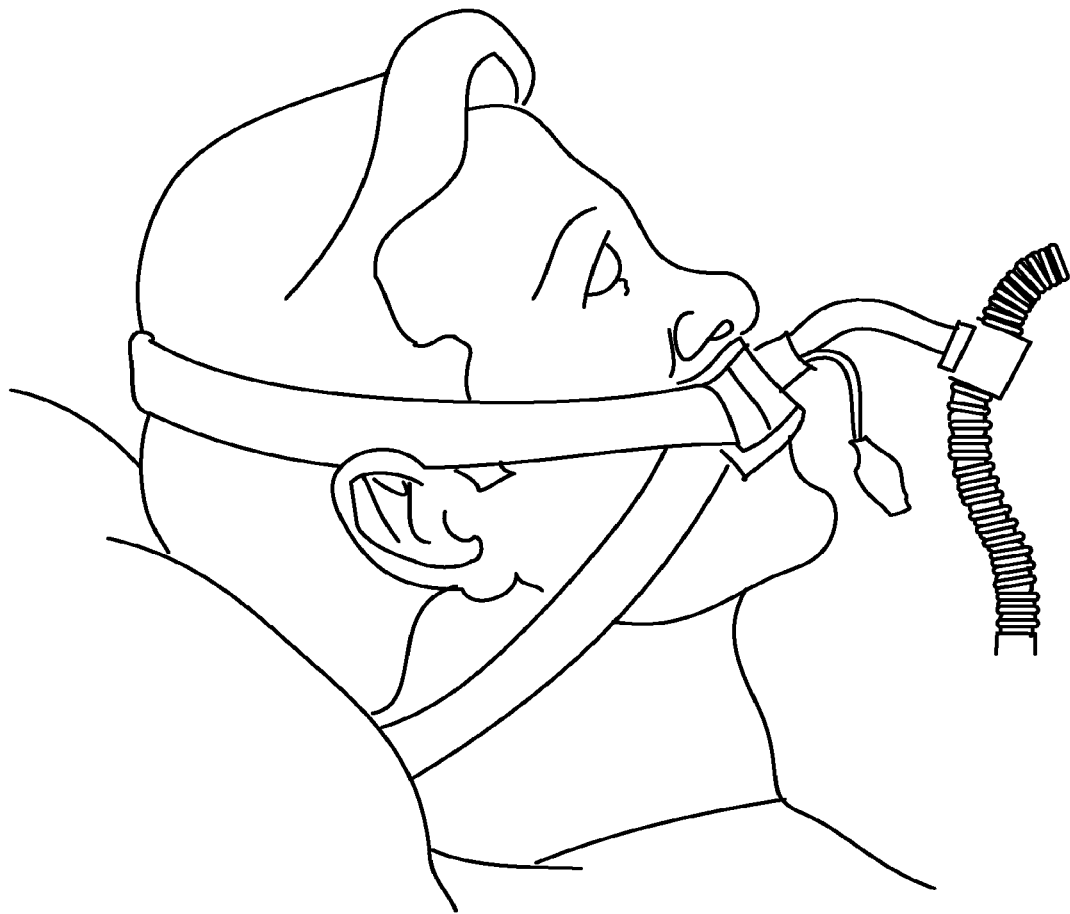
FIG. 15B shows a patient breathing with an endotracheal tube, where the patient's upper airways are bypassed.
Figure 15C:
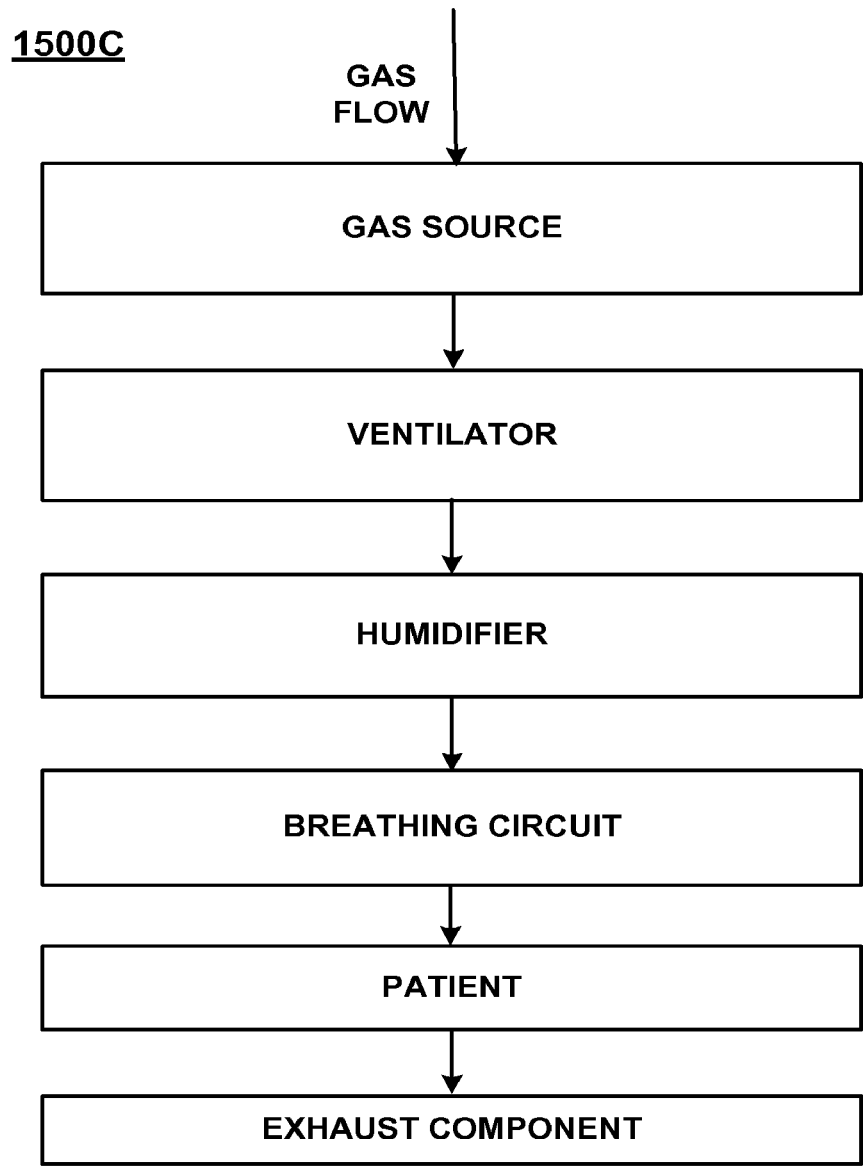
FIG. 15C illustrates a flow diagram of a flow of gas during single limb ventilation.
Figure 15D:
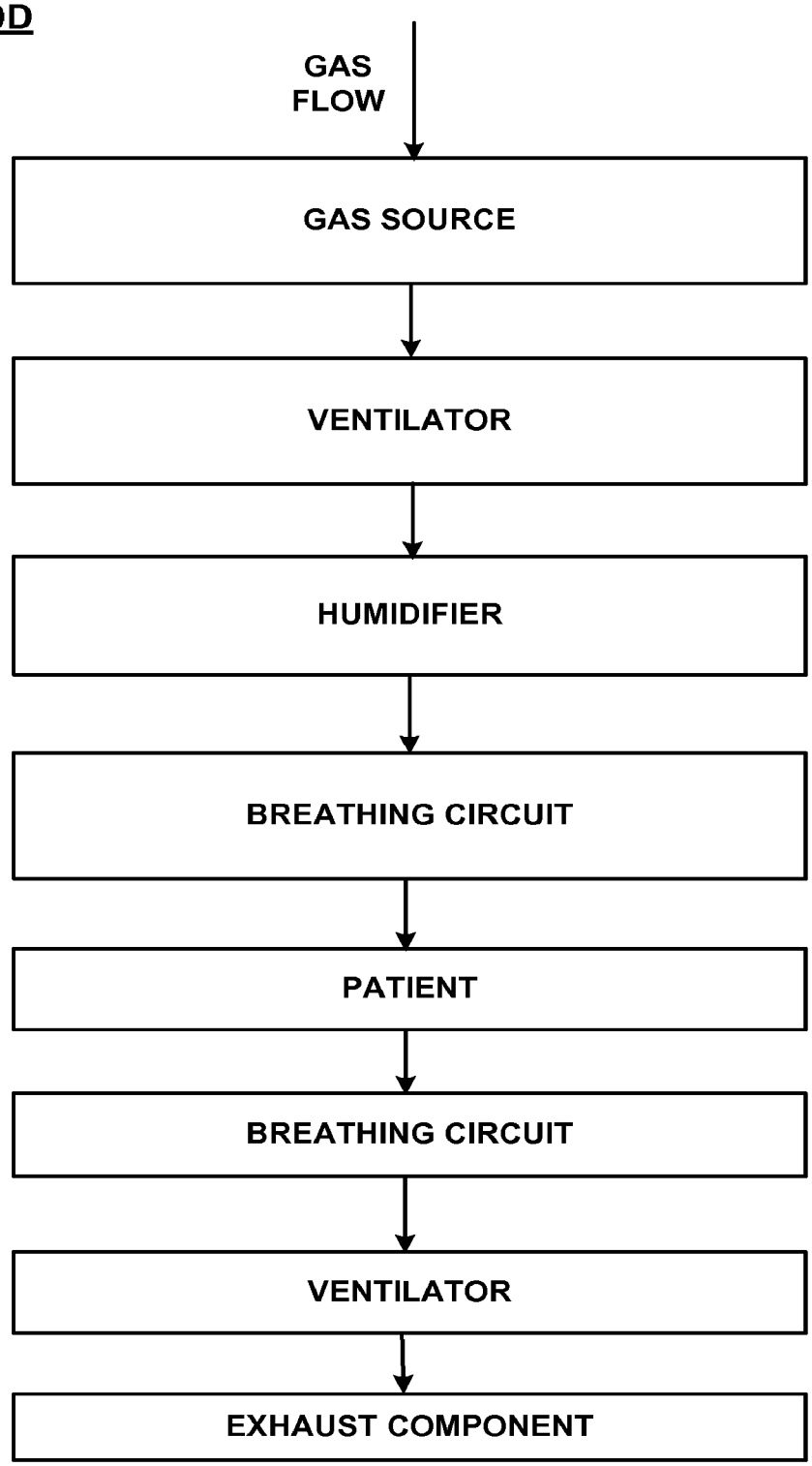
FIG. 15D illustrates a flow diagram of a flow of gas during dual limb ventilation.

Furthermore, it should be noted that the methods and devices described herein may be used in various modes of respiratory care, including, but not limited to, non-invasive single limb ventilation, dual-limb invasive ventilation, dual-limb non-invasive ventilation, continuous positive airway pressure (CPAP), bubble CPAP, bi-level positive airway pressure (BiPAP), intermittent positive pressure (IPPB), bland aerosol therapy and oxygen therapy. In general, non-invasive single and dual-limb ventilation refers to the delivery of ventilator support using a mechanical ventilator, with one or multiple limbs, connected to a mask or mouthpiece instead of an endotracheal tube. For example, FIG. 15A shows a front perspective view of a patient breathing with a mask through the upper airways (using a non-invasive ventilation system). A dual-limb invasive therapy refers to the delivery of ventilator support using a mechanical ventilator, with multiple limbs, connected to an endotracheal tube. For example, FIG. 15B illustrates a patient breathing with an endotracheal tube, wherein the patient's upper airways are bypassed (using an invasive ventilation system). Further, FIGS. 15C and 15D illustrate flow diagrams 1500C and 1500D, respectively, of the flow of gas during single limb and dual limb ventilation, respectively. More particular, 1500C of FIG. 15C, with regards to single limb ventilation, shows gas flowing from a gas source to a ventilator, to a humidifier, to a breathing circuit, to a patient, to an exhaust component. In contrast, 1500D of FIG. 15D, with regards to dual limb ventilation, shows gas flowing from a gas source to a ventilator, to a humidifier, to a breathing circuit, to a patient, to a breathing circuit, to a ventilator, to an exhaust component.

CPAP refers to the maintenance of positive pressure in the airway throughout a respiratory cycle. Bubble CPAP refers to a procedure that doctors use to help promote breathing in premature newborns. In bubble CPAP, positive airway pressure is maintained by placing the expiratory limb of the circuit under water. The production of bubbles under the water produces a slight oscillation in the pressure waveform. BiPAP refers to the maintenance of positive pressure during inspiration, but the reduction of positive pressure during expiration. IPPB refers to the non-continuous application of positive airway pressure when, for example, an episode of apnea is sensed. Bland aerosol therapy refers to the delivery of hypotonic, hypertonic, or isotonic saline, or sterile water in aerosolized form, to a patient as a medical intervention. Oxygen therapy refers to the delivery of oxygen to a patient, as a medical intervention.

The following discussion is divided into six sections: 1) humidifying respiratory gases; 2) maintaining a water level in a humidification component; 3A) a fluted heater wire; 3B) a capillary heater wire; 4) a non-metallic humidification component; 5) automatically setting a humidification level; and 6) other embodiments.

Section 1: Humidifying Respiratory Gases

Embodiments of present technology provide a non-contact electromagnetic radiation heating method which eliminates the need for a metallic component or conducting surface in a humidification component and simplifies the process of transferring heat to the water volume to produce water vapor. The electromagnetic radiation passes through the humidification component walls and/or through a specific transmitting surface in the humidification component.

Further, embodiments of the present technology provide a method for heating a respiratory water volume (water bath) which utilizes an electromagnetic radiation emission element or emitter to transfer heat to the water volume. The heated water volume subsequently produces water vapor at a gas-liquid interface. This water vapor is available to humidify respiratory gases being delivered to a patient. The wavelength emission range of the electromagnetic radiation emitter as well as the electromagnetic radiation transmission wavelength spectrum of the humidification component are chosen such that the water inside the component can receive sufficient energy to be heated to the point of providing sufficient vaporization for patient humidification.

In one embodiment, the electromagnetic radiation emitter may be made of ceramic or other materials known to provide electromagnetic radiation emission spectrums which are compatible with the electromagnetic radiation absorption spectrum of water. Similarly, the material of construction of the humidification component is chosen to provide reasonable transmission of the target electromagnetic radiation wavelengths. For example, high density polyethylene may be used.

Electrical energy provided to the emitter is converted to electromagnetic radiation. In one embodiment, but not limited to, the electromagnetic radiation is an infrared (IR) emission. IR emission from the IR emitter is passed through the walls of a humidification component or a specific transmitting surface incorporated into the humidification component. IR energy transmitted through the walls is absorbed by the water inside the humidification component, which produces heat. The heated liquid water in the humidification component produces water vapor at a surface where it contacts the respiratory gases being delivered to a patient. The respiratory gases which pass through this water vapor region are humidified by the water vapor so that the patient receives humidified gas which is comfortable for breathing. In another embodiment, but not exclusive to other forms of electromagnetic radiation, the electromagnetic radiation is a microwave emission. Microwave emission from an emitter is transmitted through the walls and absorbed by the water in the same manner as described above for an IR emission.

FIG. 1 shows a device 100 for humidifying respiratory gases, in accordance with embodiments of the present technology. The device 100 includes a humidification component 102 and a heating element 110. The humidification component 102 holds a water volume 104. In embodiments, the heating element 110 converts received electrical energy 108 to electromagnetic radiation 120. The electromagnetic radiation 120 is transferred to the water volume 104, thereby heating the water volume 104.

In one embodiment, the humidification component 102 is made of cross-linked polyethylene. While in another embodiment, the humidification component 102 is blow molded. This manufacturing technique enables the humidification component 102 to be a single piece, thus providing a more simplistic design and reducing expenditures for individual components. Additionally, the one piece design of a blow molded humidification component 102 makes it almost impossible for a liquid leak to occur. Of note, a "single piece" refers to one continuous piece of material, or more than one piece of material that are attached to each other in such a way to appear seamless. In yet another embodiment, the humidification component 102 is disposable.

In one embodiment, the heating element 110 is positioned independent of the humidification component 102. The term, "independent", refers to a non-contact position. For example, the heating element 110 does not directly touch the humidification component 102.

In one embodiment, the heating element 110 is integrated within a base unit 106, while the base unit 106 is coupled with the humidification component 102 and the heating element 110. In one embodiment, the base unit 106 supports the humidification component 102 at its base 112. For example, but not limited to such example, in one embodiment, the humidification component 102 rests on top of the base unit 106, such that the heating element 110 does not touch the humidification component 102. In another embodiment, the humidification component 102 is attached to the base unit 106 at an attachment point other than at the base 112. However, the base unit 106 is still supporting the base 112, as well as other portions, of the humidification component 102.

Further, in one embodiment, the heating element 110 is positioned such that it is inaccessible to a user during use of the device 100, thus protecting the user from the heat of the heating element 110. For example, the heating element 110 may be integrally positioned within the base unit 106 such that, while the humidification component is placed atop the base unit 106, the heating element 110 remains unexposed to the user during use. Since the heating element 110 is integral to the base unit 106, in one embodiment, the heating element 110 may be reused for the same patient or for another patient, even though the humidification component 102 is discarded.

In various embodiments, the heating element 110 is, but is not limited to one of the following: an IR emitter; and a microwave emitter. The heating element 110, as the IR emitter, includes ceramic material, according to one embodiment.

In one embodiment, the electromagnetic radiation 120 is transferred to the water volume 104 through at least a portion of the humidification component 102. The water volume 104 is consequently heated up, producing water vapor.

During the operation of device 100, respiratory gases flow across the heated water volume 104. The water vapor 114 interacts with the respiratory gases, thereby humidifying the respiratory gases. In one embodiment, the humidification component 102 includes a fluid inlet 116 and a fluid outlet 118. The respiratory gases flow above the water volume 104, entering the humidification component 102 at the fluid inlet 116 and exiting the humidification component 102 as humidified gases at the fluid outlet 118.

In one embodiment, the electromagnetic radiation 120 is transferred to the water volume 104 through a wall of the humidification component 102. Referring to FIG. 1, it can be seen that in one embodiment, the electromagnetic radiation 120 is transferred through the base 112 of the humidification component 102. However, in another embodiment, the electromagnetic radiation 120 is transferred through the ceiling and/or a side wall of the humidification component 102.

In another embodiment and as described herein, the at least a portion of the humidification component 102 through which the electromagnetic radiation 120 is transferred is transmissive to the electromagnetic radiation 120, by being a transmissive surface, such as an IR transmissive polymer, like a high density polyethlylene. Of note, in one embodiment, the portion of the humidification component 102 is of an inexpensive highly transmissive material that is disposable. While in another embodiment, the transmissive surface is made of an expensive material that is not disposable, but which may be cleaned and reused. In embodiments of the present technology, the selection of transmissive materials to be used for the humidification component 102 is dependent at least on its transmissivity, thickness and melting point.

In one embodiment, the electromagnetic radiation 120 is in an IR and/or a microwave spectrum. In one embodiment, the humidification component 102 includes reflective surfaces within, wherein the reflective surfaces direct the electromagnetic radiation 120 to the humidification component 102.

In yet another embodiment, the device 100 is used with a legacy device, to heat up standing water that might be present, for example, in the inspiratory/expiratory circuits within the breathing circuit.

Figure 2:
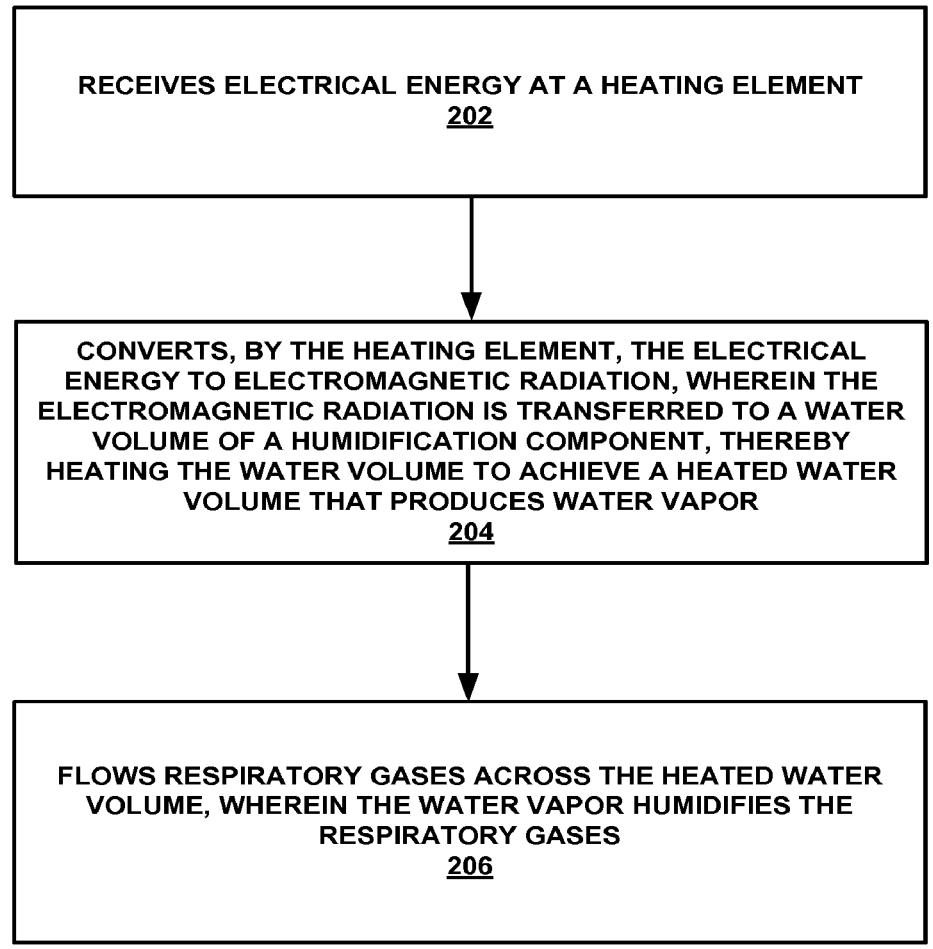
FIG. 2 is a flow diagram of an example method for humidifying respiratory gases, in accordance with embodiments of the present technology.

FIG. 2 is a flow diagram of a method 200 for humidifying respiratory gases, in accordance with embodiments of the present technology.

At 202 and as described herein, method 200 includes receiving electrical energy 108 at a heating element 110, the heating element 110. The electrical energy 108 received by the heating element 110 heats up the heating element 110, which in turn gives off electromagnetic radiation 120, for example, IR wavelengths within a certain range. Some of these IR wavelengths represent an energy desired for heating the water volume 104. While other IR wavelengths are not sufficient to heat the water volume 104. The electromagnetic radiation 120 needed is a function of at least the absorption rate of the water volume 104 and the transmissivity of the material of the humidification component 102.

At 204 and as described herein, method 200 includes converting, by the heating element 110, the electrical energy 108 to electromagnetic radiation 120. The electromagnetic radiation 120 is transferred to the water volume 104 through at least a portion of the humidification component 102. Thus, a water volume 104 is heated. The water volume 104 that is heated produces water vapor 114.

At 206 and as described herein, method 200 includes flowing respiratory gases across the water volume 104 that is heated, wherein the water vapor 114 humidifies the respiratory gases.

Figure 3A:
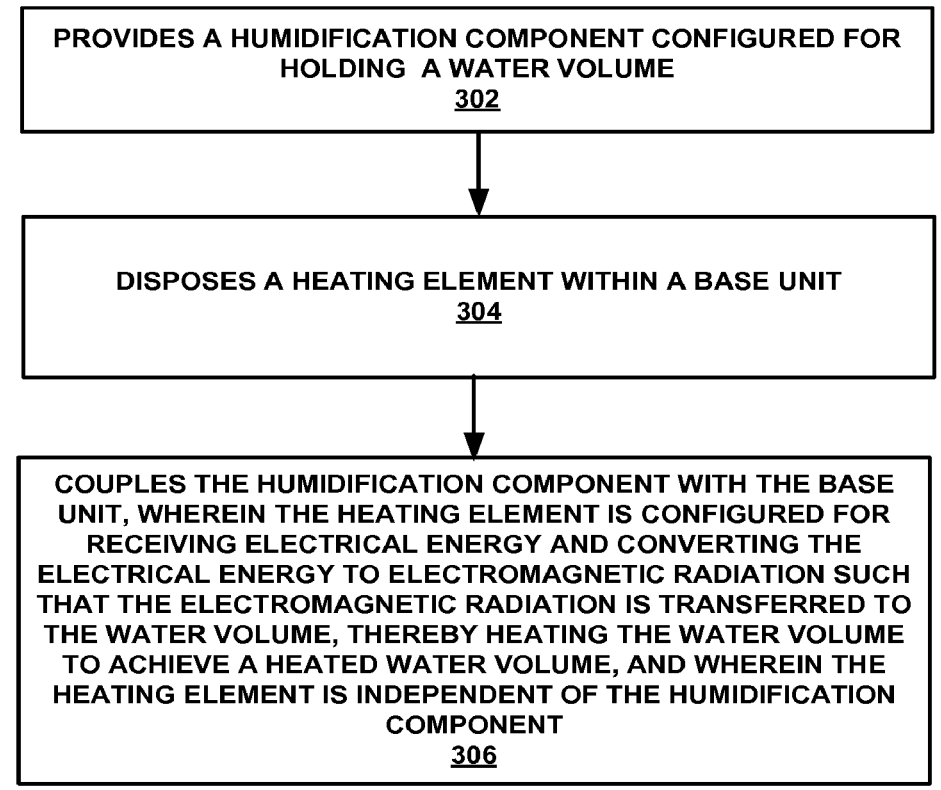
FIG. 3A is a flow diagram of an example method for manufacturing a device for humidifying respiratory gases, in accordance with embodiments of the present technology.

FIG. 3A is a flow diagram of a method 300A for manufacturing a device 100 for humidifying respiratory gases, in accordance with an embodiment of the present technology.

At 302 and as described herein, method 300A includes providing a humidification component 102 that holds a water volume 104.

At 304 and as described herein, method 300A includes disposing the heating element 110 within a base unit 106.

At 306 and as described herein, method 300A includes coupling the humidification component 102 with the base unit 106, wherein the heating element 110 receives electrical energy 108 and converts the electrical energy 108 to electromagnetic radiation 120 such that the electromagnetic radiation 120 is transferred to the water volume 104. The water volume 104 is thus heated to become a heated water volume. Additionally, the heating element 110 is independent of the humidification component 102.

Figure 3B:
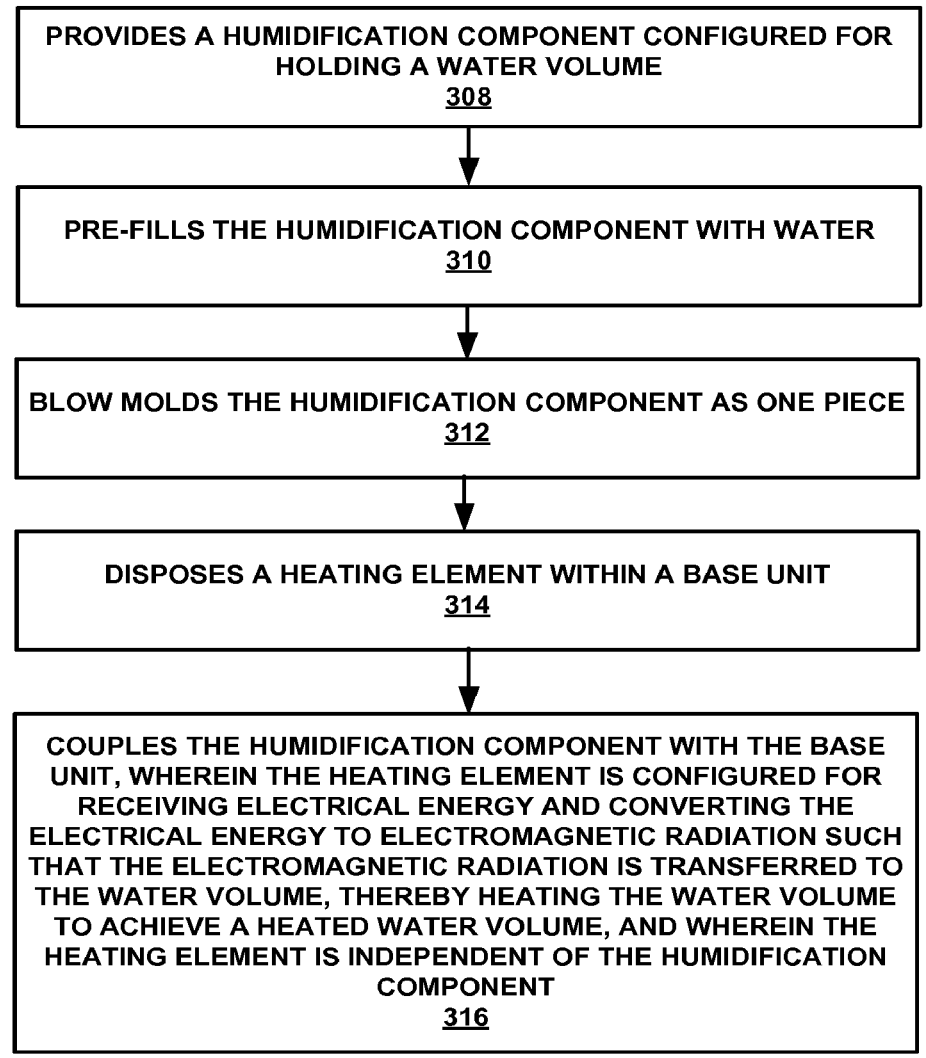
FIG. 3B is a flow diagram of an example method for manufacturing a device for humidifying respiratory gases, in accordance with embodiments of the present technology.

FIG. 3B is a flow diagram of a method 300B for manufacturing a device 100 for humidifying respiratory gases, in accordance with an embodiment of the present technology.

At 308 and as described herein, method 300B includes providing a humidification component 102 that holds a water volume 104, according to one embodiment of the present technology.

At 310 and as described herein, method 300B includes pre-filling the humidification component 102 with water, according to one embodiment. For example, before the device 100 is shipped to the retailer, user, etc., the humidification component 102 is pre-filled with inhalation grade water. By utilizing a pre-filled humidification component 102, humidification therapy is applied to a patient more quickly than having to first assemble the humidification component 102, spike the water bag, and then fill the humidification component 102.

At 312 and as described herein, method 300B includes blow molding the humidification component 102 as one piece, according to an embodiment of the present technology.

At 314 and as described herein, according to one embodiment, method 300B includes disposing the heating element 110 within a base unit 106.

At 316 and as described herein, according to one embodiment, method 300B includes coupling the humidification component 102 with the base unit 106, wherein the heating element 110 receives electrical energy 108 and converts the electrical energy 108 to electromagnetic radiation 120 such that the electromagnetic radiation 120 is transferred to the water volume 104. The water volume 104 is thus heated to become a heated water volume. Additionally, the heating element 110 is independent of the humidification component 102.

It should be appreciated that the steps of methods 300A and 300B may be performed in an order different than that shown, and the illustration therein is not intended to limit the order of the steps within either method 300A or 300B to that shown in FIGS. 3A and 3B.

Section 2: Maintaining a Water Level in a Humidification Component

Existing state-of-the-art respiratory humidifiers maintain a desired water level within a humidification chamber using internal float components which physically move up and down with the water level, occluding a water filling valve opening when the water level rises and opening a water filling valve when the level drops. The presence of these float geometries within the humidification chamber complicates manufacturing and adds cost to the disposable portion of the humidifier. It additionally occupies gas volume and reduces the water surface area available for heat transfer and vapor production. Furthermore, since the floats may cause damage to the ceiling geometry or valve and water filling components when bumping up and down while being shipped, additional expense is incurred in creating a retaining geometry that keeps the floats from moving during shipping.

Embodiments of the present technology aim to maintain a water level within a humidification component without using components internal to the humidification component. This allows for a much simpler manufacturing process, which is also less costly. Furthermore, this allows for a completely unobstructed water surface which is then available for transferring heat and mass with the passing respiratory gas. Instead of sensing the water's existence, and ultimately the water level, and using floats that are thrown away with each chamber, embodiments of the present technology use at least one sensor, such as an optical or capacitive sensor(s), which may be conserved for a second use or second patient. Of note, in one embodiment, only one sensor is used. While in another embodiment, multiple sensors are used.

In one embodiment, these sensors are incorporated into a base unit which is external to the humidification component. In this way, the sensors do not occupy any space within the humidification component and do not get discarded with each disposable humidification component. The addition of a plurality of sensors coupled with the base unit also enables the knowledge of the water level to be incorporated into the control logic for the humidifier. This provides advantages, such as the ability to calculate other types of information, that existing systems do not offer. For example, existing systems use energy and temperature calculations to compute a lack of water in a humidification component. However, an embodiment of the present technology uses a plurality of sensors and light to compute a water level or a lack of water.

Thus, embodiments of the present technology utilize components that remain external to the humidification component to provide a device and method for automatically filling and maintaining the water level in a humidification component. A water level control element, such as a pinch valve or other similarly functioning valve, is actuated using signals from sensors (e.g., optical sensors, capacitive sensor) which are disposed external to the humidification component. In this manner, the humidification component contains only water and does not require internal water leveling sensors and/or components, such as floats.

In one embodiment, an optical transmitter and optical receiver are placed in diametrically opposed positions around the humidification component. The amount of light sensed by the optical receiver from the optical transmitter is dependent upon whether there is water present between these sensors. When the water level in the humidification component is sufficiently high, the water level control element remains closed. When the water level drops, this is sensed as an increase in the amount of light received at the optical receiver. Each time the optical receiver achieves a target signal level associated with this condition, an integrated water level control element, such as a pinch valve, is signaled to open, which refills the humidification component to the desired target level.

In another embodiment, a capacitive sensor is used to sense the water level in the humidification component and activate or deactivate the water level control element. In another embodiment, a reflective optical sensor is utilized to sense the water level in the humidification component and activate or deactivate the water level control element. Other types of external sensors capable of achieving the same results of activating and deactivating a water level control element may also be used. Further, redundant secondary and even tertiary water level sensors may also be used as "fail safes", just in case the first set of sensors fail and cause danger to the patient and/or damage to the humidification system.

Thus, embodiments of the present technology provide a device for automatically filling and maintaining a desired water level in a respiratory humidifier. The device incorporates components, such as at least one sensor and a water level control element, which are positioned external to the humidification component. The water level is sensed using the at least one sensor (optical or capacitive sensor[s]) which provide the necessary signals to open and/or close an integrated water level control element.

Figure 4:
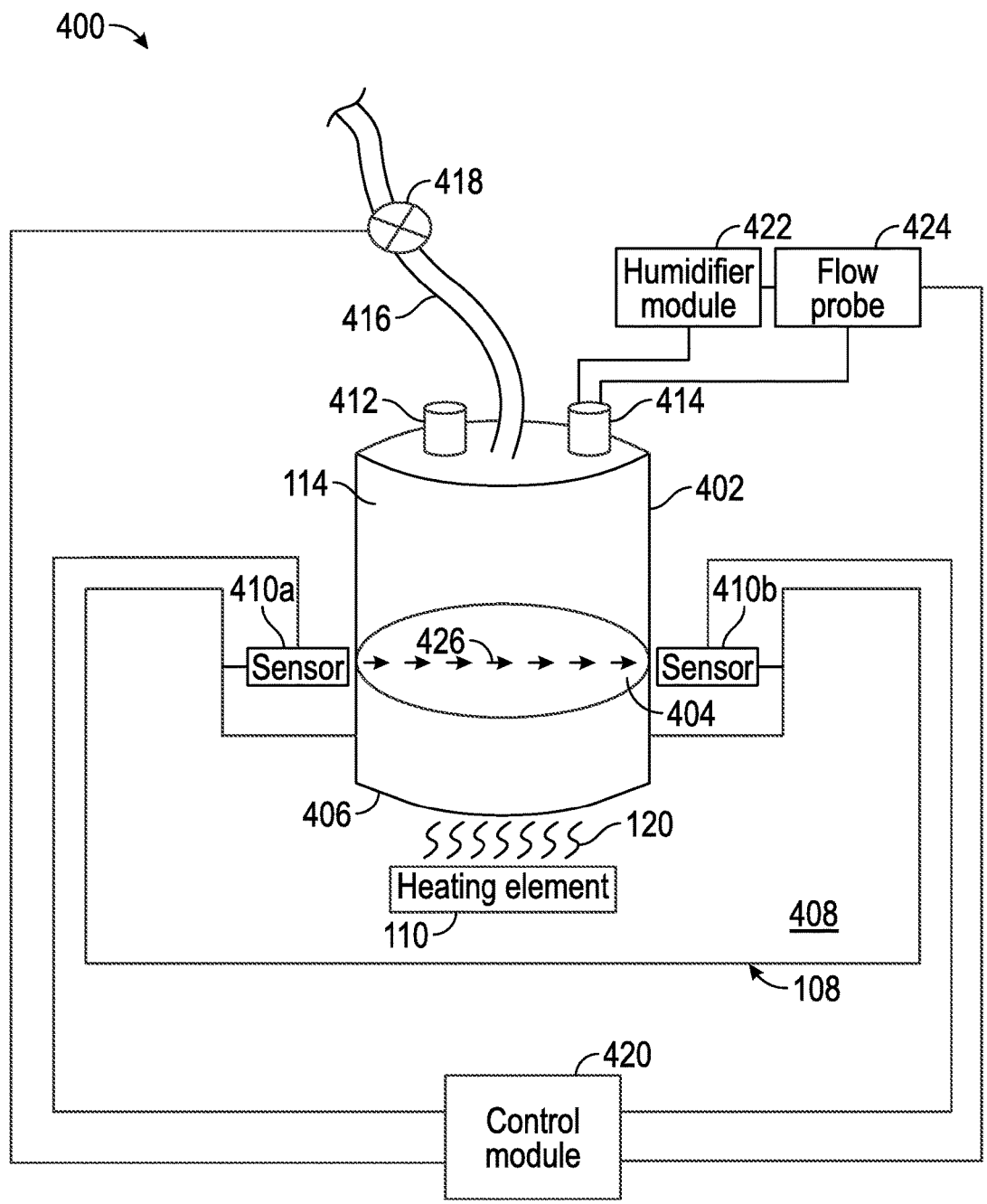
FIG. 4 shows a device for maintaining a water level in a humidification component, in accordance with embodiments of the present technology.

FIG. 4 shows a device 400 for maintaining a water level in a humidification component 402, in accordance with an embodiment of the present technology. The device 400 includes at least one sensor 410a and 410b (hereinafter, "at least one sensor 410" unless otherwise noted) positioned external to a humidification component 402 and coupled with a control module 420. It should be appreciated that the at least one sensor 410 may include more sensors than just sensors 410a and 410b. However, for purposes of brevity and clarity, only two sensors are shown herein. It should also be noted that an embodiment of the present technology includes only one sensor, such as sensor 410a.

The at least one sensor 410 senses water related information in the humidification component and provides the water related information to the control module 420. The water related information includes data that is used to control an operation of a water level control element 418. In one embodiment, based on at least the water related information, the lack of water or an excess amount of water in the humidification system may be detected, wherein the humidification system includes the humidification component 402.

In one embodiment, the at least one sensor 410 is independent of the humidification component 402. As discussed herein, the at least one sensor, in one embodiment, includes at least one primary sensor and at least one redundant sensor. Furthermore, the at least one sensor, in one embodiment, is an optical sensor and/or a capacitive sensor. In another embodiment, the optical sensor includes a transmissive sensor and/or a reflective sensor.

FIG. 4 shows, in one embodiment, the humidification component 402 coupled through a coupling mechanism (not shown) with the base unit 408. The coupling mechanism couples a portion of the base unit 408 with a portion of the humidification component 402. In one embodiment, the at least one sensor 410, also coupled with the base unit 408, is positioned external to the humidification component 402. As such, the at least one sensor 410 is not attached to the humidification component 402. The water level control element 418 is shown coupled with the humidification component 402 via a water filling line 416. The water level control element 418 is also coupled with the control module 420.

The humidification component 402 holds a water volume 404. In one embodiment, the base unit 408 is coupled with the humidification component 402, as well as supporting the base 406 of the humidification component 402 (as already described herein).

In one embodiment, the control module 420 utilizes the water related information to control the operation by the water level control element 418 that maintains a target water level in the humidification component 402. In one embodiment, the operation controlled is that of opening the water level control element 418 and/or closing the water level control element 418. Furthermore, in another embodiment, the water related information includes data configured for being used by the control module 420 to compute an output of the humidification system and a quantity of water consumed by the humidification system.

In one embodiment, the water level control element 418 is coupled with the humidification component 402 and controls the flow of water into the humidification component 402. In one embodiment, the water level control element 418 is coupled with the humidification component 402 by being attached to a water filling line 416. The water filling line 416 is in turn attached to the humidification component 402. In embodiments of the present technology, the water level control element 418 includes, but is not limited to the following structures: a single pinch valve; multiple pinch valves; a peristaltic pump; a piezo pump; a valve, and a duct.

Pinch valves are commonly known in the art. It should be appreciated that any valving mechanism may be used that is capable of being coupled with the humidification component 402, via a device 400 that is or has functioning similar to the water level control element 418 described herein, is capable of being coupled with the control module 420 and responding to the control module 420's instructions. Thus, the functioning of the water level control element 418 is controllable by and at the control module 420.

According to one embodiment of the present technology, the control module 420 directs the water level control element 418 to self-adjust to meet a water level objective. The water level objective is that water level, determined prior to or during the use of the device 400, which is desired to be maintained within the humidification component 402. This determination of the desired water level may be the result of many factors, including but not limited to: the patient's needs; the functionality of the device 400 itself; and the respiratory gases used. The water level control element 418, in one embodiment, is controlled by the control module 420 by receiving an "adjustment" instruction from the control module 420, such that the following of this adjustment instruction results in the humidification component 402 achieving the desired water level objectives. Further, in one embodiment, the adjustment instruction is based on the water related information (discussed below) received by the control module 420 from the at least one sensor 410, as well as the water level objective.

In one embodiment and as discussed herein, the adjustment instruction includes an instruction to do at least one of, but not limited to, the following: open the water level control element 418; close the water level control element 418; adjust the opening of the water level control element 418 at a predetermined rate of speed; and to partially open and/or close the water level control element 418 at a desired distance.

In one embodiment, the at least one sensor 410 is coupled with the control module 420 and the base unit 408 and is positioned external to the humidification component 402. The at least one sensor 410 is an optical sensor. The at least one sensor 410 senses an amount of light 426 in the humidification component 402 and transmits signals associated with the amount of light to the control module 420. For example, the sensor 410a (a transmitter as applied to this example) transmits the light 426 across the humidification component 402. The sensor 410b (a receiver as applied to this example) detects the light 426 transmitted. The sensors 410a and 410b then transmit signals to the control module 420 regarding having transmitted and detected the light 426.

In one embodiment, and as described herein, the at least one sensor 410 are optical sensors, such as, but not limited to, reflective optical sensors and transmissive sensors. The reflective optical sensors determine an amount of reflected light in the humidification component 402. Light or IR energy is directed towards the humidification component 402. The reflective sensors sense the amount of light or IR energy that bounces back, thereby collecting "water related information" regarding the water level as well.

Transmissive sensors, on the other hand, in one embodiment, are placed on both sides of the humidification component 402. The transmissive sensors sense the amount of the light or IR energy that makes it through the humidification component 402, thereby also collecting "water related information" regarding the water level within the humidification component 402. In another embodiment, an optical transmitter and optical receiver of the optical sensors are placed in diametrically opposed positions around the humidification component 402.

In one embodiment and as discussed herein, the at least one sensor 410 includes a set (of at least two) of primary sensors, a set (of at least two) of redundant secondary sensors, and/or even a set (of at least two) of redundant tertiary sensors. These redundant sets of sensors provide a "fail safe", just in case the primary and/or the secondary set of sensors fail.

In various embodiments, the at least one sensor 410 may be disposed and arranged in various orientations on the base unit 408, as well as being proximate to the humidification component 402. (The term, "proximate", refers to a position that is near enough, and still being external to, the humidification component 402, to enable the functioning of the at least one sensor 410 as described herein.) For example, the at least one sensor 410 may be arranged such that they follow the curvature of the humidification component 402 while also being the same distance away from the base 406 of the humidification component 402. In another embodiment, the at least one sensor 410 may be arranged in a vertically stacked manner on the base unit 408, as well as being proximate to the humidification component 402. In yet another embodiment, the at least one sensor 410 may be arranged in arrays. Thus, the at least one sensor 410 may be arranged in a strategic manner such that, for example, the slant of the humidification component 402 is taken into account when determining the water level within the slanted humidification component 402.

Further, in one embodiment, the at least one sensor 410 is located above the humidification component 402. The positioning of the at least one sensor 410 above the humidification component 402, especially if the at least one sensor 410 is able to sense at the center of the humidification component 402, minimizes the effect of tilting of the humidification component 402. Moreover, in one embodiment, the at least one sensor 410 is located below the humidification component 402.

In another embodiment, the device 400 includes a flow probe 424 coupled with the fluid outlet 414. The flow probe 424 measures the amount of the humidified gases that flow out of the humidification component 402 to the patient, through the fluid outlet 414, and thus also measures the water loss occurring during such flow.

In one embodiment, the device 400 includes a humidifier module 422 that measures humidified gases delivered to a patient. Based on at least the water level calculations, the flow of humidified gas out of the fluid outlet 414 (measured from the flow probe 424) and how much respiratory gas is being passed through the humidifier module 422, the humidifier module 422 measures the amount of humidified gases that is delivered to the patient. This measurement(s) are stored at the control module 420.

FIG. 5 is a flow diagram of a method 500 for maintaining a water level in a humidification component 402 (of FIG. 4), in accordance with embodiments of the present technology.

At 502 and as described herein, in one embodiment the method 500 includes sensing, by at least one sensor 410, water related information in the humidification component 402, wherein the at least one sensor 410 is positioned external to the humidification component 402 and coupled with a control module 420.

At 504 and as described herein, in one embodiment the method 500 includes providing, by the at least one sensor 410, the water related information to the control module 420. The water related information includes data configured for being used to control an operation of a water level control element 418.

At 506 and as described herein, in one embodiment the method 500 includes maintaining a target water level in the humidification component 402, based on the water related information of 504. The maintaining the target water level in the humidification component 402 at 506, includes opening and/or closing the water level control element 418.

At 508 and as described herein, in one embodiment the method 500 includes, based on at least the water related information, computing an output of the humidification system and a quantity of water consumed by the humidification system, wherein the humidification system includes the humidification component 402.

At 510 and as described herein, in one embodiment the method 500 includes, based on at least the water related information, detecting a lack of water or detecting an excess amount of water in the humidification system, wherein the humidification system includes the humidification component 402.

FIG. 6 is a flow diagram of a method 600 for manufacturing a device 400 for maintaining a water level in a humidification component 402 (of FIG. 4), in accordance with embodiments of the present technology.

At 602 and as described herein, method 600 includes providing a humidification component 402 that holds a water volume 404.

At 604 and as described herein, method 600 includes coupling at least one sensor 410 with a control module 420. The at least one sensor 410 is enabled to sense water related information in the humidification component 402 and is enabled to provide the water related information to the control module 420. The water related information includes data that is capable of being used by the control module 420 to control an operation of a water level control element 418. The at least one sensor 410 is positioned external to the humidification component 402.

Furthermore, in one embodiment, the coupling of the at least one sensor 410 with the control module 420 includes coupling at least one primary sensor and at least one redundant sensor with the control module 420, wherein the at least one primary and redundant sensor make up the at least one sensor 410.

Example Computer System Environment

Figure 7:
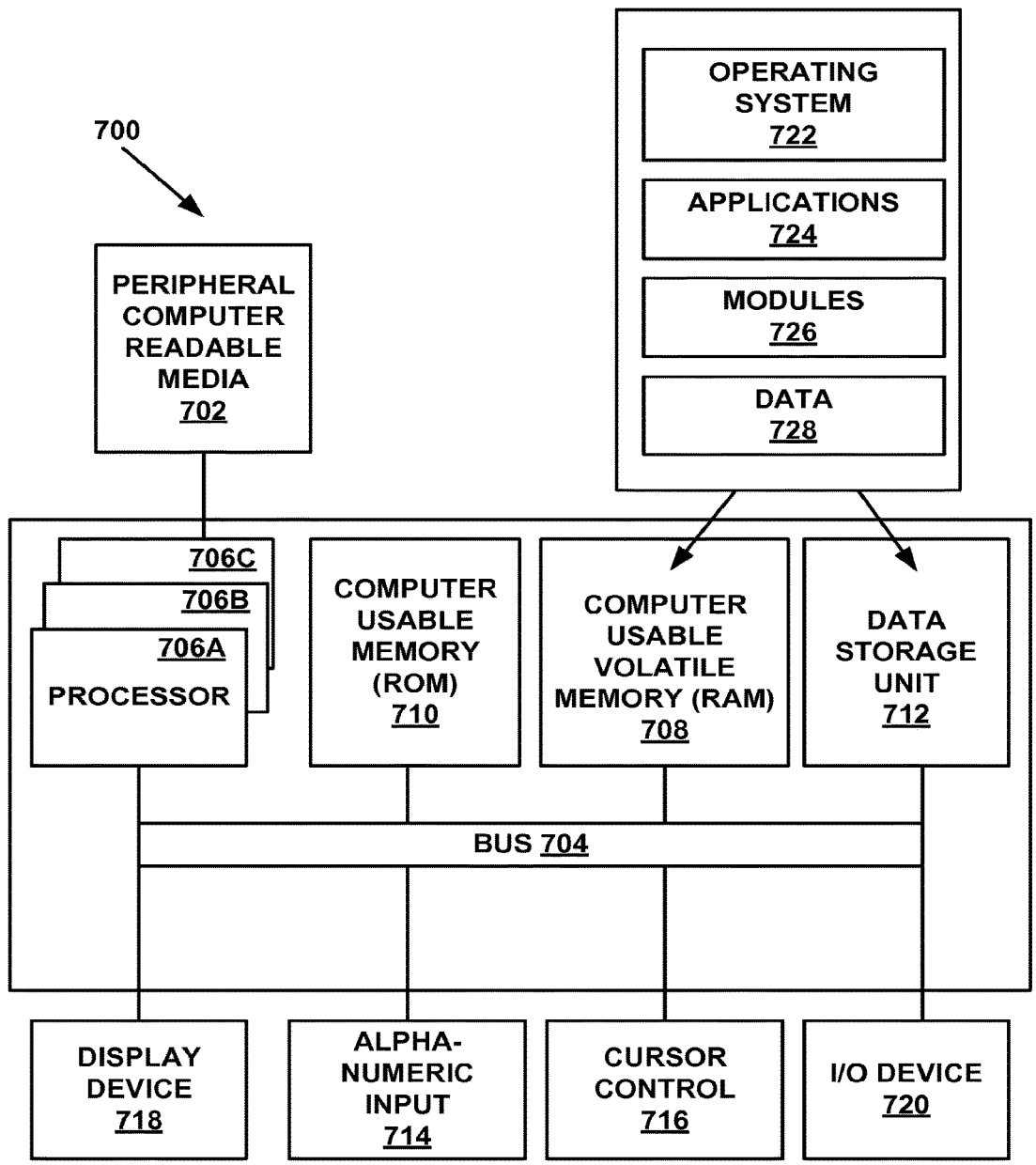
FIG. 7 is a diagram of a computer system used for the method for maintaining a water level in a humidification component, in accordance with embodiments of the present technology.

With reference now to FIG. 7, portions of the technology for: the sensing of 502, the providing of 504, the maintaining of 506 and the computing of 508 are composed of computer-readable and computer-executable instructions that reside, for example, in computer-readable storage media of a computer system. That is, FIG. 7 illustrates one example of a type of computer that can be used to implement embodiments, which are discussed below, of the present technology.

FIG. 7 illustrates a computing system 700 used in accordance with embodiments of the present technology. In one embodiment, computing system 700 is the same as the control module 420 shown in FIG. 4. Further, in another embodiment, module 726 is the same as control module 420 shown in FIG. 4. It is appreciated that system 700 of FIG. 7 is an example only and that the present technology can operate on or within a number of different computer systems including general purpose networked computer systems, embedded computer systems, routers, switches, server devices, user devices, various intermediate devices/artifacts, stand alone computer systems, and the like. As shown in FIG. 7, computing system 700 of FIG. 7 is well adapted to having peripheral computer readable media 702 such as, for example, a floppy disk, a compact disk, a flash memory, and the like coupled thereto.

System 700 of FIG. 7 includes an address/data bus 704 for communicating information, and a processor 706A coupled to bus 704 for processing information and instructions. As depicted in FIG. 7, system 700 is also well suited to a multi-processor environment in which a plurality of processors 706A, 706B, and 706C are present. Conversely, system 700 is also well suited to having a single processor such as, for example, processor 706A. Processors 706A, 706B, and 706C may be any of various types of microprocessors. System 700 also includes data storage features such as a computer usable volatile memory 708, e.g. random access memory (RAM), coupled to bus 704 for storing information and instructions for processors 706A, 706B, and 706C.

System 700 also includes computer usable non-volatile memory 710, e.g. read only memory (ROM), coupled to bus 704 for storing static information and instructions for processors 706A, 706B, and 706C. Also, a data storage unit 712 (e.g., a magnetic or optical disk and disk drive) coupled to bus 704 for storing information and instructions may be in system 700. System 700 also may include an input device 714, that in one embodiment, may include alphanumeric and/or function keys coupled to bus 704 for communicating information and command selections to processor 706A or processors 706A, 706B, and 706C. System 700 also may include an optional cursor control device 716 coupled to bus 704 for communicating user input information and command selections to processor 706A or processors 706A, 706B, and 706C. System 700 of the present embodiment also may include an optional display device 718 coupled to bus 704 for displaying information.

Referring still to FIG. 7, optional display device 718 of FIG. 7 may be a liquid crystal device, cathode ray tube, plasma display device or other display device suitable for creating graphic images and alphanumeric characters recognizable to a user. Optional cursor control device 716 allows the computer user to dynamically signal the movement of a visible symbol (cursor) on a display screen of display device 718. Many implementations of cursor control device 716 are known in the art including a trackball, mouse, touch pad, joystick or special keys on alpha-numeric input device 714 capable of signaling movement of a given direction or manner of displacement. Alternatively, it will be appreciated that a cursor can be directed and/or activated via input from alpha-numeric input device 714 using special keys and key sequence commands.

System 700 is also well suited to having a cursor directed by other means such as, for example, voice commands. System 700 may also include an I/O device 720 for coupling system 700 with external entities. For example, in one embodiment, I/O device 720 is a modem for enabling wired or wireless communications between system 700 and an external device and/or network such as, but not limited to, the Internet.

Referring still to FIG. 7, various other components are depicted for system 700. Specifically, when present, an operating system 722, applications 724, modules 726, and data 728 are shown as typically residing in one or some combination of computer usable volatile memory 708, e.g. random access memory (RAM), and data storage unit 712. However, it is appreciated that in some embodiments, operating system 722 may be stored in other locations such as on a network or on a flash drive; and that further, operating system 722 may be accessed from a remote location via, for example, a coupling to the internet. In one embodiment, the present technology, for example, is stored as an application 724 or module 726 in memory locations within RAM 708 and memory areas within data storage unit 712. The present technology may be applied to one or more elements of described computing system 700.

The computing system 700 is only one example of a suitable computing environment and is not intended to suggest any limitation as to the scope of use or functionality of the present technology. Neither should the computing environment of computing system 700 be interpreted as having any dependency or requirement relating to any one or combination of components illustrated in the computing system 700.

The present technology may be described in the general context of computer-executable instructions, such as program modules, being executed by a computer. Generally, program modules include routines, programs, objects, components, data structures, etc., that perform particular tasks or implement particular abstract data types. The present technology may also be practiced in distributed computing environments where tasks are performed by remote processing devices that are linked through a communications network. In a distributed computing environment, program modules may be located in both local and remote computer-storage media including memory-storage devices and/or non-volatile memory within a microcontroller device.

Section 3A: Fluted Heater Wire

Breathing circuits are utilized to deliver such medical support as air and anesthetics from a machine that creates an artificial environment to a patient via tubes. Breathing circuits are used in surgical procedures, respiratory support and respiratory therapies. For example, in a most general case, breathing circuits include an inspiratory limb running from a ventilator to a patient and an expiratory limb running from the patient back to the ventilator.

The ventilator pushes gas through the inspiratory limb to reach the patient. The patient inhales this pushed gas and exhales gas into the expiratory limb. For purposes of the present technology, any portion of the breathing circuit could be considered a patient circuit or conduit. It should be appreciated that the present technology is well suited to be used in any portion of the patient circuit or any other respiratory gas conduit.

If the gas is cold when the patient inhales it, the patient's body works hard to try to warm up the gas for ease of breathing. Humidity can also be added to the circuit, because when someone is intubated for ventilation, the body's natural humidification process is bypassed. In normal breathing, the upper airways heat and humidify inspired gas, and recover heat and humidity from exhaled gas, thereby conserving body heat and water. Due to the intubation (bypassing upper airways), there is a humidity deficit which creates serious physiological problems if not addressed (e.g., through use of a humidified circuit, or heat and moisture exchanger).

When gas is humidified, the temperature in the tube must be kept above the dew point to prevent condensation within the tube. Thus, breathing circuits can be designed with heating wires positioned within the interior of at least the inspiratory limb, or patient circuit.

If a heating wire is positioned within the respiratory gas conduit such that the heating wire stretches the full length of the inspiratory limb, then all of the gas moving through the inspiratory limb becomes heated. Thus, the gas arriving from the inspiratory limb into the patient's airway is also well heated.

One of the challenges associated with providing active humidification to a patient is managing condensation (commonly known in the industry as "rainout") in the patient circuit limbs. Several known approaches to managing condensation include collecting the condensation in known locations (water traps), heating the circuit limbs with a heater wire (heated circuits) and diffusing the water through a porous wall.

Respiratory circuits can accumulate condensation in a concentrated area that then becomes a site that fosters even greater condensation generation. An example of this phenomena would be a person accidently knocking the circuit, compelling condensation to accumulate at the lowest circuit elevation. This pool of condensation is cooler than the surrounding saturated respiratory gas, facilitating the saturated gas to condense into an even larger pool of condensation, growing with every breath of saturated gas that passes by. The problem can even progress to the point that all the respiratory gases are forced through the liquid, further exacerbating the problem.

Embodiments of the present technology self-correct the condensation problem by utilizing a fluted heater wire. Grooves (or "flutes") are disposed on the heater wire to create a geometry that is conducive to encouraging capillary action. In one example, the grooves are disposed on the sheath of the heater wire. The surface energy of the heater wire can be modified with technology common to the art, such as plasma treatment.

The combination of favorable geometry and a high surface energy (low contact angles) will enable the heater wire present in a respiratory gas conduit to evaporate any condensation with which the wire comes in contact. A heater wire with a helical pattern increases the likelihood that any pooling condensation will be in contact with the heater wire, thereby becoming evaporated. Thus, embodiments of the present technology provide a device for removing excess condensation from a breathing circuit, and more particularly, in one embodiment, a respiratory gas conduit.

Figure 8:
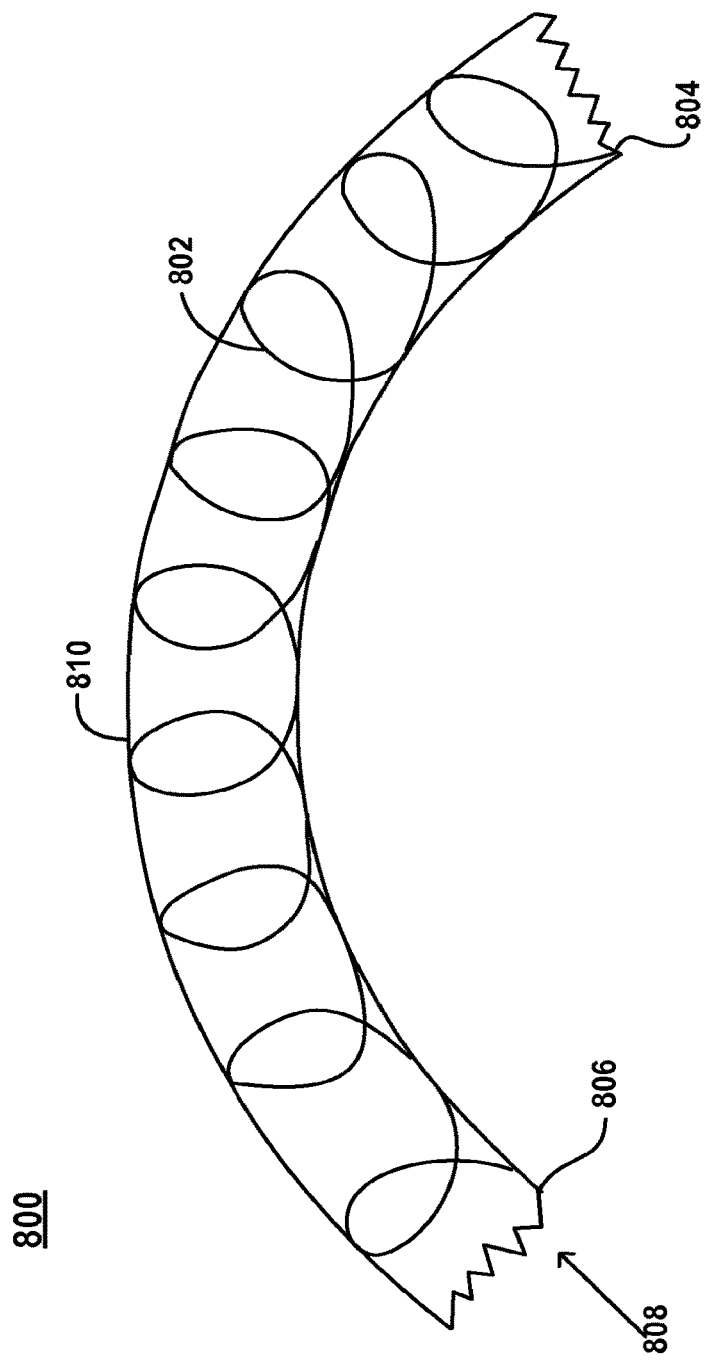
FIG. 8 shows a portion of a breathing circuit, in accordance with embodiments of the present technology.

FIG. 8 shows a portion of a breathing circuit 800, in accordance with an embodiment of the present technology. The breathing circuit 800 includes a respiratory gas conduit 810, a heater wire 802 disposed inside the respiratory gas conduit 810 and sheathing 902 (shown in FIG. 9A and discussed below) as part of the heater wire 802. Of note, the heater wire 802, in one embodiment, is a heating component that heats (increases the temperature) the gas 808 inside the respiratory gas conduit 810. The respiratory gas conduit 810 receives gas 808 at an input end 806 and delivers the gas 808 through an output end 804. In one embodiment, the gas 808 is delivered to a patient through the output end 804. However, in another embodiment, the gas 808 leaves the patient, moving from the input end 806, and arrives at the exhaust and/or ventilator at the output end 804. The heater wire 802 heats the gas 808 inside the respiratory gas conduit 810 between the input end 806 and the output end 804.

Figure 9A:
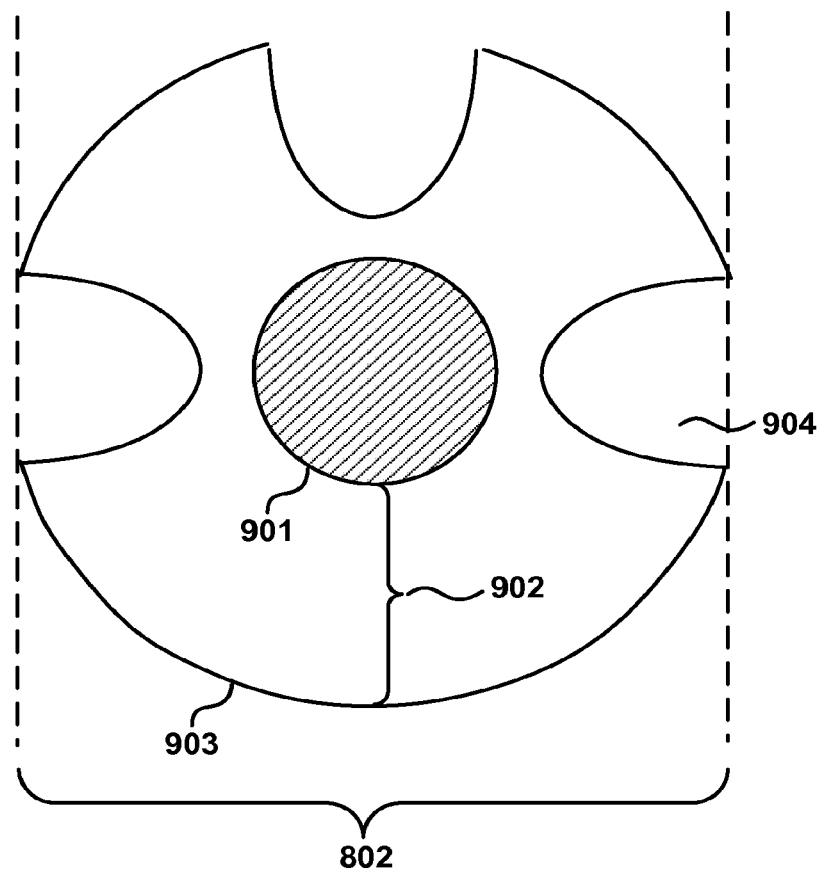
FIG. 9A shows a cross-sectional view of a heater wire with at least one groove disposed thereon, in accordance with embodiments of the present technology.

FIG. 9A shows a device 900A in cross-sectional view, for removing condensation from a breathing circuit 800, such as that breathing circuit 800 shown in FIG. 8, in accordance with an embodiment of the present technology. The device 900A includes the heater wire 802 that includes at least one groove 904, wherein the heater wire 802 is to be positioned in the respiratory gas conduit 810. The heater wire 802 includes a sheathing 902 surrounding the wire component 901 within the heater wire 802. The sheathing 902 includes at least one groove 904 disposed thereon. The at least one groove 904 wicks up water that has formed in a condensation region within the respiratory gas conduit 810 and then transports the wicked up water to a re-evaporation region. Of note, while one groove 904 is shown in FIG. 9A, it should be appreciated that there may be more than one groove disposed on the heater wire 802. Further, it should be appreciated that there are various descriptions of methods for disposing at least one groove on the heater wire 802, such as but not limited to, "forming", "pressing out" and "extruding".

In one embodiment, the sheathing 902 is insulation material. Further, the insulation material, in one example, has a smooth external coating 903, interrupted by the at least one groove 904. In other words, the wire component 901 is coated with insulation material as at least a portion of the sheathing 902. The surface of the coating 903, opposite that surface in contact with the wire component 901, is smooth, except for the grooves that are disposed through the sheathing 902 (or, as in this example, the insulation material).

In one embodiment, the re-evaporation region is a hot surface along the heater wire 802. For example, the condensation region is considered to be cooler region, or a place at which the water accumulates and does not evaporate. Once the water is wicked up into the at least one groove 904 integral with the sheathing 902, the water is transported along the groove away from the condensation region and to a hotter region along the heater wire 802 where the water is able to once again evaporate, or "re-evaporate".

In one embodiment, the sheathing 902 includes, but is not limited to, one or more of the following additives: hydrophilic; antifogging; and antistatic. It should be appreciated that when the sheathing 902 includes the hydrophilic additive, the combination of the at least one groove 904 and the sheathing 902 more quickly and efficiently wicks the water up along the at least one groove 904 and away from the condensation region. In one embodiment, the sheathing 902 is, either partially or wholly, of a material that has an inherently high surface energy.

In one embodiment, the at least one groove 904 includes, but is not limited to, one or more of the following shapes: a V-shape; a square shape; a semi-circular shape; a non-uniform shape; and a combination of the foregoing shapes. As discussed herein, it should be appreciated that there may be any number of grooves disposed on the sheathing 902. For example, in one embodiment, there are six grooves equally spaced around the wire component 901 and disposed on the sheathing 902. However, in another embodiment, these grooves are not equally spaced. Further, in one embodiment, the at least one groove 904 extends along the direction of an extended sheathing 902 and thus wire component 901.

It should be appreciated that the geometry of the at least one groove 904 is such that the width of the at least one groove 904 is desired to be as small as possible and the length of the at least one groove 904 is desired to be as big as possible. Further, the contact angle between the at least one groove 904 and the water is desired to be as close to zero as is possible, while still functioning to wick up as much water as desired. In other words, the contact angle between the at least one groove 904 and the water is desired to be that of a low contact angle, which is obtained by utilizing a high surface energy. Water is thereby caused to be drawn, through capillary action, towards an unwetted part of the at least one groove 904. Moreover, embodiments of the present technology provide for continuous wicking up of the water from a condensation region.

Figure 9B:
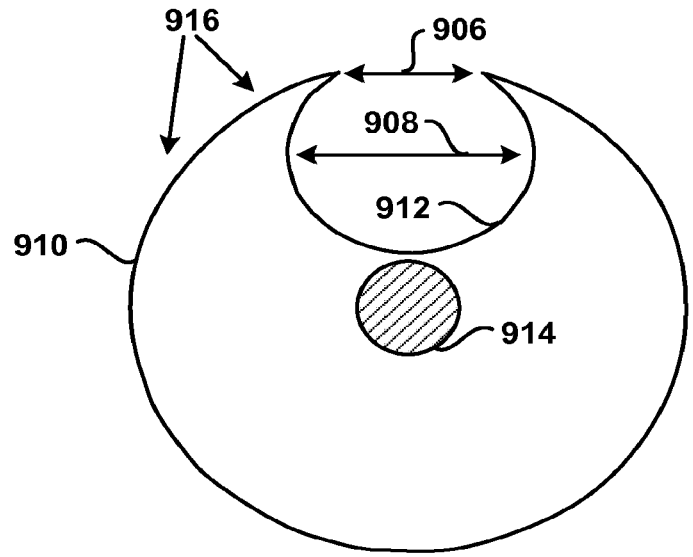
FIG. 9B shows a cross-sectional view of a heater wire with at least one groove disposed thereon, in accordance with embodiments of the present technology.

FIG. 9B shows a device 900B in cross-sectional view, for removing condensation from a breathing circuit 800, such as the breathing circuit 800 shown in FIG. 8, in accordance with an embodiment of the present technology. The device 900B includes a heater wire 910 (including a wire component 914 and a sheathing [not labeled]) with at least one groove 912 disposed thereon, in accordance with an embodiment of the present technology. In one embodiment, the first width 906 of the at least one groove 912 at a surface 916 of the heater wire 910 is less than a second width 908 of the at least one groove 912. The second width 908 is a maximum width of the at least one groove 912, when viewed in cross-section (as is shown in FIG. 9B).

FIG. 10 is a flow diagram of a method 1000 for automatically removing condensation from a breathing circuit 800, in accordance with an embodiment of the present technology.

Referring now to FIGS. 8-10, at 1002 and as described herein, method 1000 includes wicking up water from a condensation region within a respiratory gas conduit 810 of the breathing circuit 800. The wicking up of water is performed by at least one groove 904 disposed on a heater wire 802, wherein the heater wire 802 is positioned within the respiratory gas conduit 810.

At 1004 and as described herein, method 1000 includes transporting, by the at least one groove 904, the wicked up water from the condensation region to a re-evaporation region. As described herein, this wicking action is the result of a capillary process that is driven by the high energy surface (from a low contact angle) between the at least one groove 904 and the water.

At 1006 and as described herein, method 1000 includes evaporating the wicked up water by a hot surface of the heater wire 802.

Figure 11:
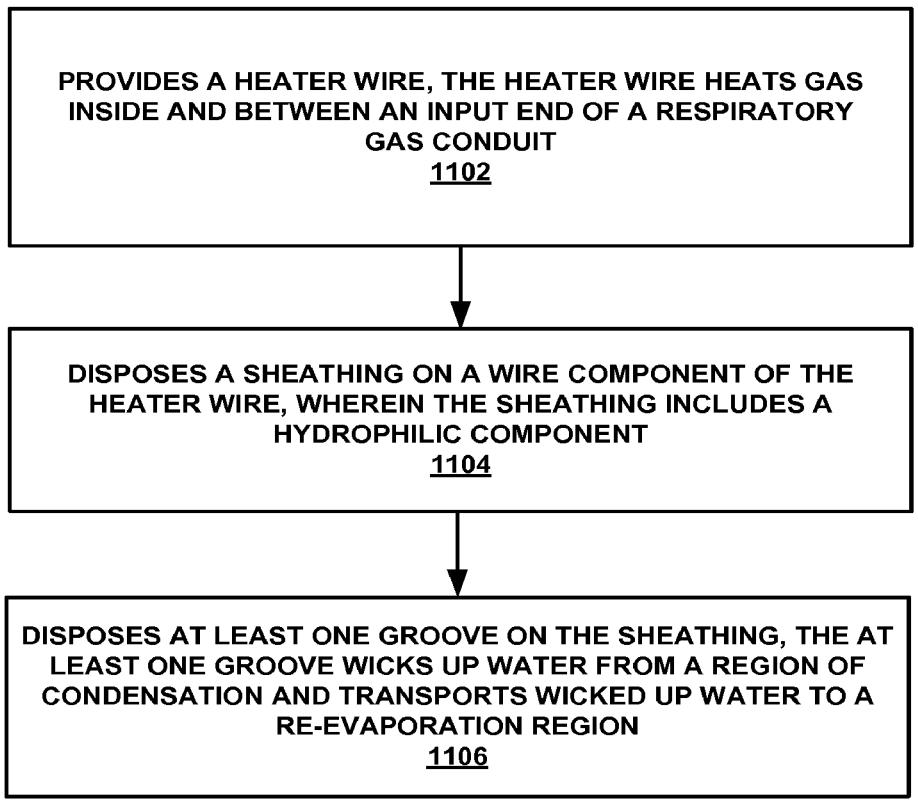
FIG. 11 is a flow diagram of an example method for manufacturing a device for removing condensation from a breathing circuit, in accordance with embodiments of the present technology.

FIG. 11 is a flow diagram of a method 1100 for manufacturing a device 900 for removing condensation from the breathing circuit 800. Referring now to FIGS. 8-9B and 11, at 1102 and as described method 1100 includes providing a heater wire 802 that heats gas 808 inside and between an input end 806 and an output end 804 of an respiratory gas conduit 810. Of note, in one embodiment, the respiratory gas conduit 810 receives gas 808 at the input end 806 and delivers the gas 808 to the patient at the output end 804.

At 1104 and as described herein, method 1100 includes disposing a sheathing 902 on a wire component 901 of the heater wire 802, wherein the sheathing 902 includes a hydrophilic component.

At 1106 and as described herein, method 1100 includes disposing at least one groove 904 on the sheathing 902. The at least one groove 904 wicks up water from a region of condensation within the respiratory gas conduit 810 and transports the wicked up water to a re-evaporation region. In embodiments, the disposing of grooves of the at least one groove 904 at 1106 includes, but is not limited to, one or more of the following groove shapes: V-shape; square shape; semi-circular shape; and a combination of the foregoing shapes. Further, in one embodiment and as described herein, six grooves may be disposed thereon.

Furthermore, in one embodiment, the disposing of the at least one groove 904 includes a first width at a surface of the heater wire 802 that is less than a second width of the at least one groove 904, wherein the second width is a maximum width of the at least one groove 904, when viewed in cross-section. Moreover, It should be appreciated that in one embodiment, the disposing 1106 the at least one groove 904 on the sheathing 902 includes disposing a plurality of groove on the sheathing.

Furthermore, in one embodiment, an antifogging additive and/or an antistatic additive is added to the sheathing 902. Yet in another embodiment, the manufacturing method 1100 includes a plasma treatment.

Section 3B: Capillary Heater Wire

In one embodiment, threads are braided and/or woven around the outer geometry of a heater wire. The spaces between the threads provide a small enough geometry to facilitate capillary action. The threads employed may be, but are not limited to being, polyester. In one embodiment, lateral extensions are added to the braid and/or weave on the exterior of the heater wire. The addition of these lateral extensions facilitate water contact that is located in the convolute of the circuit limb and normally not accessible by the heater wire.

In yet another embodiment, a hollow core shell with fibers positioned in close proximity to each other form an inter-fiber capillary pathway. This hollow core shell is positioned over the insulated heater wire, wherein the insulated heater wire includes at least one lateral extension of construction similar to that of the hollow core shell of fibers.

Lateral extensions, according to embodiments, reduce contact angle requirements to further facilitate capillary action by producing smaller capillary geometry than the geometry described in section 3A regarding the fluted heater wire. Moreover, no (or a lower amount) of additives, surface treatments, and/or coatings are used, as compared to that used with the fluted heater wire embodiments. Thus, later extensions further facilitate a system and method of using capillary action to transport condensation to a hotter portion of the heater wire and re-evaporate it.

Figure 16A:
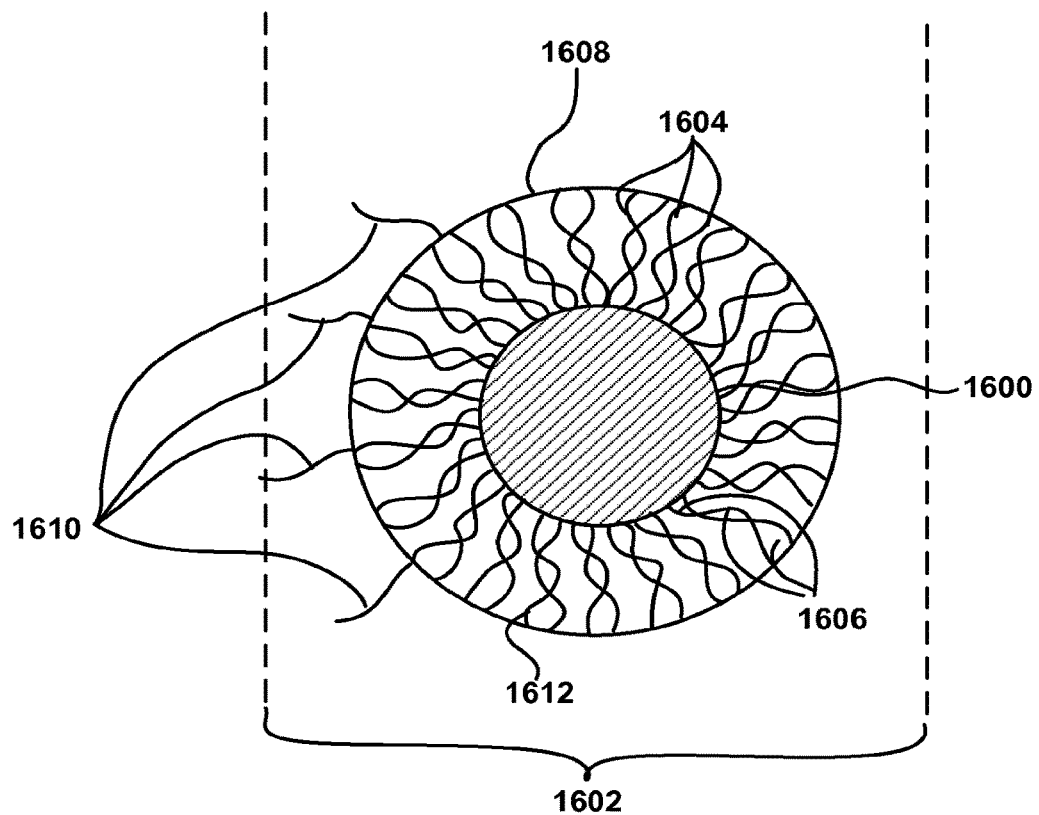
FIG. 16A shows a cross-sectional view of a heater wire with at least one extending component disposed thereon, in accordance with embodiments of the present technology.

FIG. 16A shows a cross-sectional view of a heater wire 1602 with at least one extending component 1612 disposed thereon, in accordance with embodiments. The heater wire 1602 is positioned within the respiratory gas conduit 810 (of FIG. 8) of the breathing circuit 800. Further, the heater wire 1602 includes a wire component 1600. In one embodiment, the at least one extending component 1612 is a fiber.

In one embodiment, the at least one extending component 1612 includes a braided portion 1604. In one embodiment, the at least one extending component 1612 further includes a first plurality of channels 1606 positioned within the braided portion 1604. The first plurality of channels 1606 facilitate a movement of liquid. It should be appreciated that the "liquid" noted herein with regards to various embodiments, is water in one instance. The first plurality of channels 1606 assist in the movement of liquid to a hotter portion of the heater wire 1602, where the liquid is then re-evaporated.

In one embodiment, the heater wire 1602 includes a first set of lateral extensions 1610 coupled with a surface 1608 of the braided portion 1604, wherein the surface 1608 faces away from the wire component 1600 within the heater wire 1602. The first set of lateral extensions 1610 facilitate liquid contact located in the convolute of the limb of the breathing circuit 800. It should be appreciated that the first set of lateral extensions 1610 may include just one lateral extension or a plurality of lateral extensions.

Figure 16B:
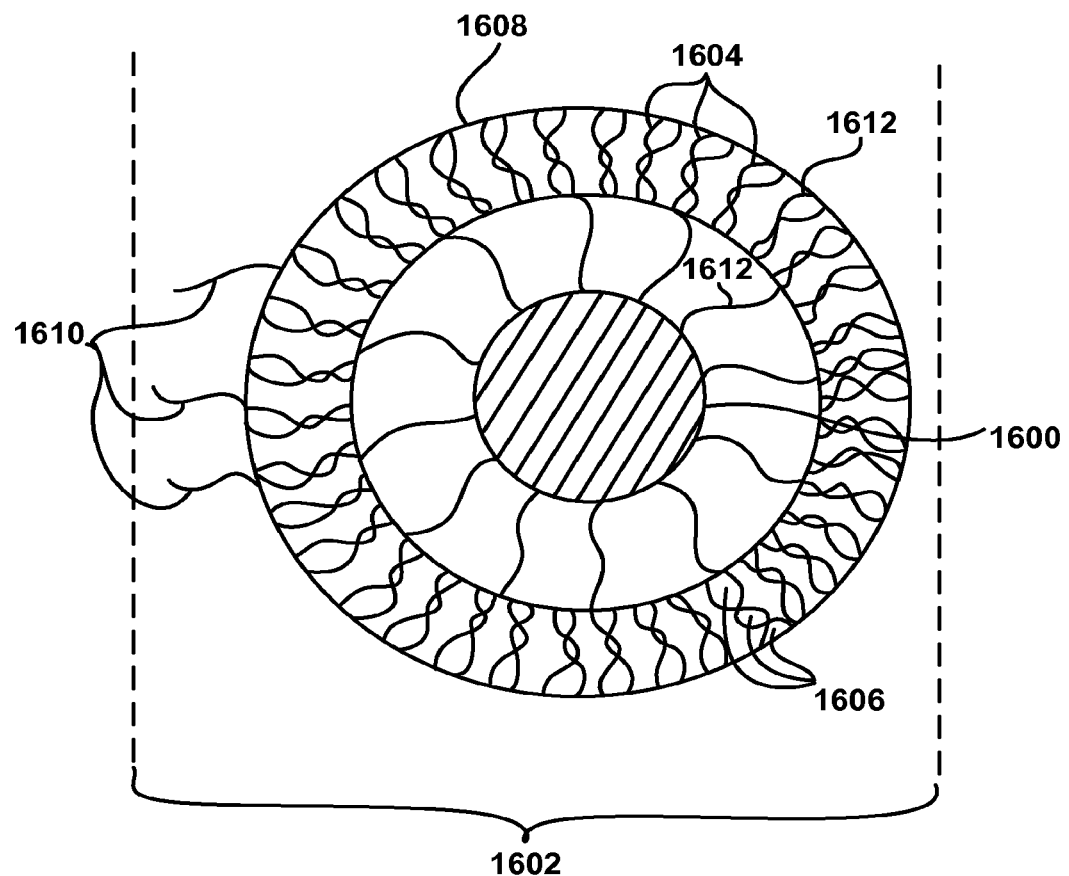
FIG. 16B shows a cross-sectional view of a heater wire with at least one extending component disposed thereon, in accordance with embodiments.

FIG. 16B shows a cross-sectional view of a heater wire 1602 with at least one extending component 1612 disposed thereon, in accordance with embodiments. As shown, the braided portion 1604 occurs as a hollow shell positioned at a distance away from the wire component 1600. However, at least one extending component 1612 is coupled with the wire component 1600 and the braided portion 1604. Of note, the braided portion 1604 includes a plurality of extending components 1612. Of note, in one embodiment, the heater wire 1602 includes a sheathing surrounding the wire component 1600, as is described herein with reference to the heater wire 802. In one example, the sheathing is of an insulation material.

Figure 17A:
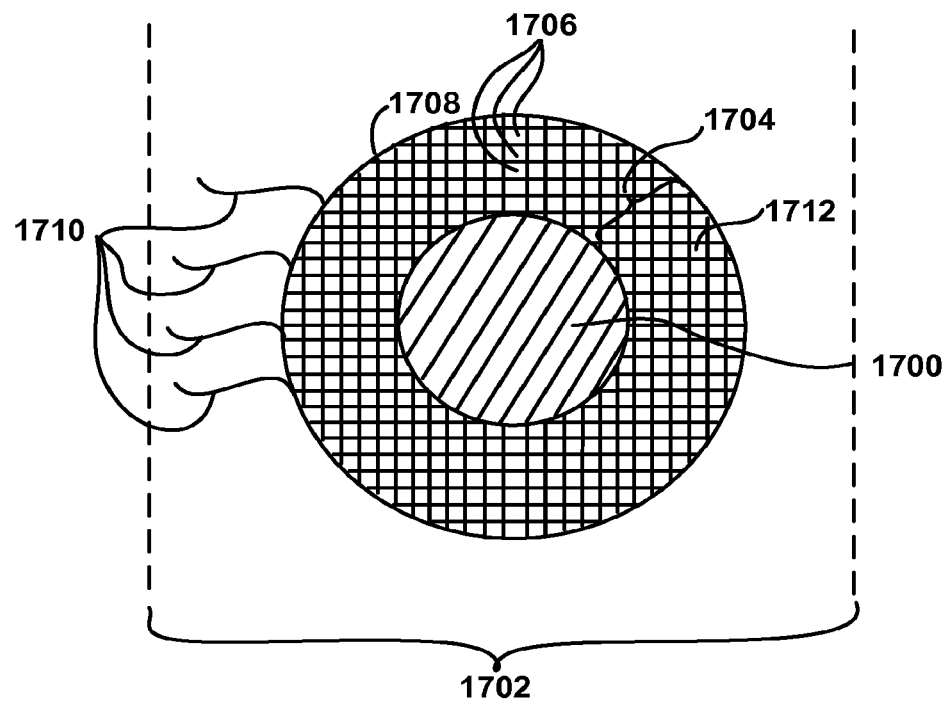
FIG. 17A shows a cross-sectional view of a heater wire with at least one extending component disposed thereon, in accordance with embodiments of the present technology.

FIG. 17A shows a cross-sectional view of a heater wire 1702 with at least one extending component 1712 disposed thereon, in accordance with embodiments. The heater wire 1702 is positioned within the respiratory gas conduit 810 (of FIG. 8) of the breathing circuit 800. Further, the heater wire 1702 includes a wire component 1700. In one embodiment, the at least one extending component 1712 is a fiber.

In one embodiment, the at least one extending component 1712 includes a woven portion 1704 and a second plurality of channels 1706 positioned within the braided portion 1704. The second plurality of channels 1706 facilitates a movement of liquid. For example, the second plurality of channels 1706 assists in the movement of liquid to a hotter portion of the heater wire 1702, where the liquid is then re-evaporated.

In one embodiment, the heater wire 1702 includes a second set of lateral extensions 1710 coupled with a surface 1708 of the woven portion 1704, wherein the surface 1708 faces away from the wire component 1700 within the heater wire 1702. The second set of lateral extensions 1710 facilitates liquid contact located in the convolute of the limb of the breathing circuit 800. It should be appreciated that the second set of lateral extensions 1710 may include just one lateral extension or a plurality of lateral extensions.

Figure 17B:
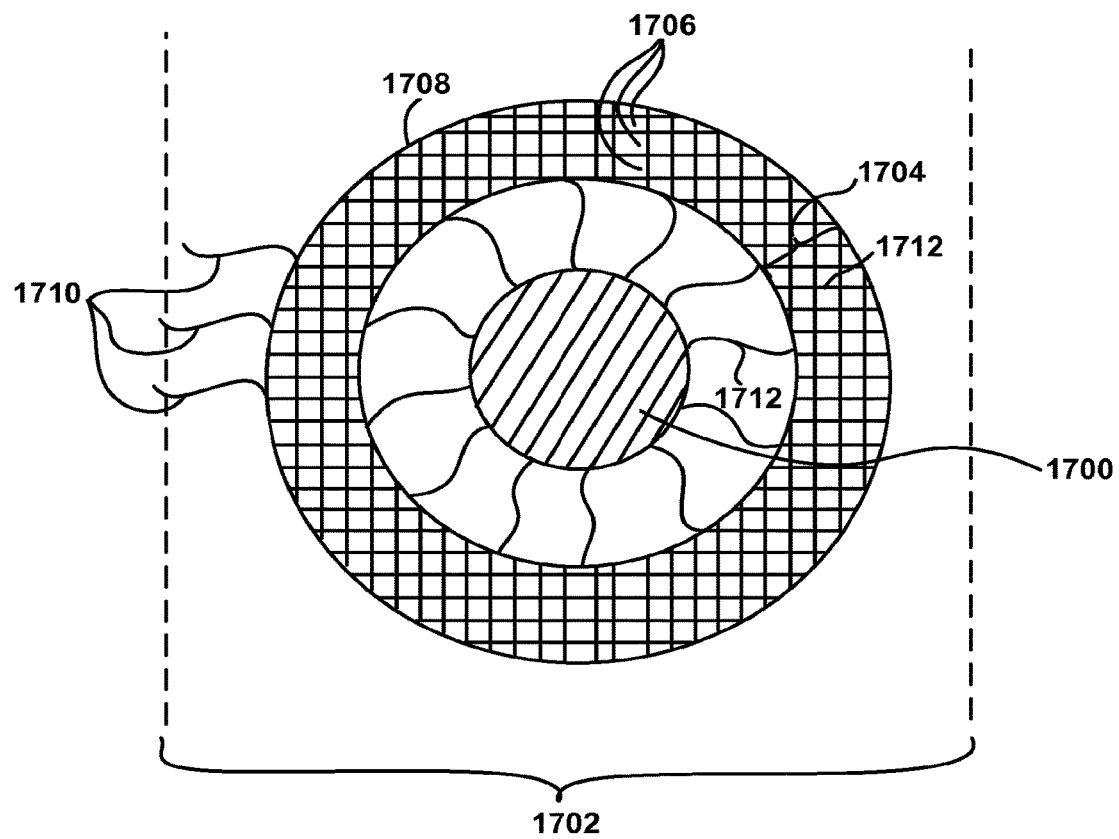
FIG. 17B shows a cross-sectional view of a heater wire with at least one extending component disposed thereon, in accordance with embodiments of the present technology.

FIG. 17B shows a cross-sectional view of a heater wire 1702 with at least one extending component 1712 disposed thereon, in accordance with embodiments. As shown, the braided portion 1704 occurs as a hollow shell positioned at a distance away from the wire component 1700. However, at least one extending component 1712 is coupled with the wire component 1700 and the braided portion 1704. Of note, the braided portion 1704 includes a plurality of extending components 1712. Of note, in one embodiment, the heater wire 1702 includes a sheathing surrounding the wire component 1700, as is described herein with reference to the heater wire 802. In one example, the sheathing is of an insulation material.

Figure 18:
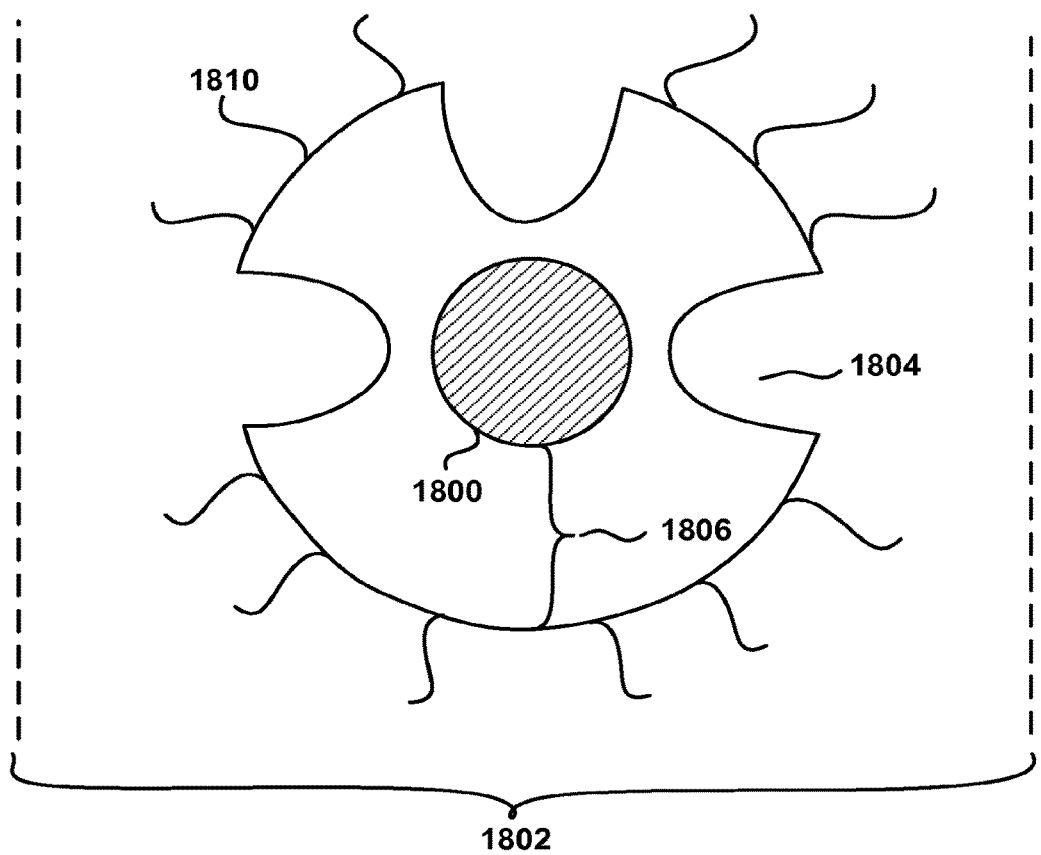
FIG. 18 shows a cross-sectional view of a heater wire with at least one extending component and one groove disposed thereon, in accordance with embodiments of the present technology.

FIG. 18 shows a cross-sectional view of a heater wire 1802 with at least one extending component 1810 and at least one groove 1804 disposed thereon, in accordance with embodiments. The at least one groove 1804 has the features of the at least one groove 904 of FIG. 9A, described herein. Furthermore, the heater wire 1802 includes, in one embodiment, a sheathing 1806, having the features of the sheathing 902 described herein For example, in one embodiment, the sheathing 1806 is insulation material. In one example, the insulation material has a smooth external coating, interrupted by the at least one groove 1804. The heater wire 1802 includes a wire component 1800. In various embodiments and coupled therewith, the heater wire 1802 includes at least the same features of the heater wire 802 described herein.

The at least one extending component 1810 may be the extending component 1612 of FIGS. 16A and 16B and/or 1712 of FIGS. 17A and 17B, discussed herein.

FIG. 19 is a flow diagram of an example method 1900 for automatically removing excess condensation from a breathing circuit, such as breathing circuit 800, in accordance with embodiments.

Referring now to FIGS. 8-10 and 16-19, at 1905, in one embodiment and as described herein, method 1900 includes wicking up liquid from a region of condensation within a respiratory gas conduit 810 of the breathing circuit 800. The wicking up of liquid is performed by the at least one extending component 1612, 1712 or 1810 disposed on the heater wire 1602, 1702 or 1802, respectively, wherein the heater wire 1602, 1702 or 1802 is positioned within the respiratory gas conduit 810.

At 1910, in one embodiment and as described herein, the at least one extending component 1612, 1712, and/or 1810 transports the wicked up liquid from a region of condensation within the respiratory gas conduit 810 to a re-evaporation region. The re-evaporation region is that region within the breathing circuit 800 which is able to heat the liquid to the point of evaporation.

At 1915, in one embodiment and as described herein, the wicked up liquid is evaporated by a hot surface of the heater wire 1602, 1702, and/or 1802.

Figure 20:
FIG. 20 is a flow diagram of an example method for manufacturing a device for removing excess condensation from a breathing circuit, in accordance with embodiments of the present technology The drawings referred to in this description should not be understood as being drawn to scale unless specifically noted.

FIG. 20 is a flow diagram of an example method 2000 for manufacturing a device for removing condensation from a breathing circuit, in accordance with embodiments.

Referring now to FIGS. 8-10 and 16-20, at 2005, in one embodiment and as described herein, a heater wire is provided, such as but not limited to, heater wire 1600. The heater wire 1600 is capable of heating gas inside and between an input end 806 and an output end 804 of the respiratory gas conduit 810.

At 2010, in one embodiment and as described herein, at least one extending component, such as but not limited to, extending component 1612, 1712 or 1810, is disposed on the heater wire 1602, 1702 or 1802, respectively. In one embodiment and as described herein, a braided portion 1604 is disposed on the heater wire 1600, wherein the braided portion 1604 includes a plurality of channels 1606 for facilitating a movement of the liquid through the braided portion 1604. In one embodiment and as described herein, the first set of lateral extensions 1610 is coupled with the surface 1608 of the braided portion 1604, wherein the surface 1608 faces away from the wire component 1600 of the heater wire 1602.

In another embodiment and as described herein, a woven portion 1704 is disposed on the heater wire 1602, 1702 and 1802, respectively. In one embodiment and as described herein, the woven portion 1704 is disposed on the heater wire 1702, wherein the woven portion 1704 includes a plurality of channels 1706 for facilitating a movement of the liquid through the braided portion 1704. In one embodiment and as described herein, the second set of lateral extensions 1710 is coupled with the surface 1708 of the braided portion 1704, wherein the surface 1708 faces away from the wire component 1700 of the heater wire 1702.

Referring now to FIGS. 8-10 and 16-18, in one embodiment, a breathing circuit 800 includes a respiratory gas conduit 810 and a heater wire 802 with at least one extending component 612, 712 and/or 810 disposed thereon. The respiratory gas conduit 810 includes an input end 806 and an output end 804, receives gas at the input end 806, and transports the gas to the output end 804. The heater wire 802 is disposed inside the respiratory gas conduit 810 and includes at least one extending component 1612, 1712 and/or 1812 disposed thereon. The at least one extending component 1612, 1712 and/or 1810 wicks up liquid from a region of condensation within the respiratory gas conduit 810 and transports the wicked up liquid to a re-evaporation region.

In one embodiment and as described herein, the breathing circuit 800 includes a sheathing 902 and at least one groove 904 disposed on the sheathing 902. The at least one groove 904 wicks up a portion of the liquid from the region of condensation within the respiratory gas conduit 810 and transports the wicked up liquid to a re-evaporation region. In one embodiment, the re-evaporation region is a hot surface along the heater wire 1602, 1702 and/or 1802.

In one embodiment and as described herein, the at least one extending component 1612, 1712, and/or 1812 is a fiber. In one embodiment and as described herein, the at least one extending component 1612 includes a braided portion 1604. In another embodiment, the at least one extending component 1612 further includes, in addition to the braided portion 1604, a first plurality of channels 1606 within the braided portion 1604. The first plurality of channels 1606 facilitates a movement of liquid along the braided portion 1604. In another embodiment and as described herein, the at least one extending component 1712 includes a woven portion 1704. In another embodiment, the at least one extending component 1712 further includes, in addition to the woven portion 1704, a second plurality of channels 1706 within the woven portion 1704. The second plurality of channels 1706 facilitates a movement of liquid along the woven portion 1704.

Thus, embodiments of the present technology provide a respiratory humidification method which utilizes at least one extending component disposed on a heater wire to reduce the contact angle requirements, thereby facilitating the wicking up of liquid from regions of condensation within the respiratory gas conduit 810 to re-evaporation regions. The plurality of channels disposed on and between the extending components assists in the movement of the liquid along the extending components.

Section 4: Non-Metallic Humidification Component

As described herein, traditional humidification systems for respiratory gas delivery in critical care and patient care settings typically involve a humidification chamber of hot water which is used to provide vapor for humidifying the delivered gases. The method for heating this water volume is most often contact heating using a hot-plate or heating element which transfers heat to the water volume through a metallic surface which is incorporated into the humidification chamber. The presence of this metallic element or base of the humidification chamber represents significant manufacturing and material costs in comparison to the other materials used in the humidification chamber such as polymers. It also necessitates a multi-step manufacturing process that involves attachment and watertight sealing of this metallic section to a polymer section.

Embodiments of the present technology provides a heating method and apparatus which eliminates the need for a metallic component or metallic conducting surface in the water chamber and simplifies the construction of the humidification chamber and method for transferring heat to the water volume to produce vapor. Embodiments of the present technology also eliminate potential failure modes for the humidification chamber where seals and multiple components meet (e.g. leaks). Embodiments provide for a much lower cost and simplified humidification chamber design. In one embodiment, the humidification component, described herein, is made in a single piece blow-moldable form. Heat from a hot plate or other heat source is conducted directly through the conductive plastic humidification component walls into the water to be vaporized.

Further, embodiments of the present technology provide a method for humidification in a respiratory system that includes a humidification component, as is described herein, which is constructed entirely of a polymer. Such a humidification component thus constructed can conduct heat into the volume of water contained within the humidification component. Moreover, the polymer material, in embodiments of the present technology, has a high melting point and a sufficiently high glass transition temperature or heat deflection temperature such that it does not soften or degrade during typical heating.

The all-polymer humidification component may be placed directly on a hot plate such as that used in existing humidifier systems and the heat is then transferred to the water by conduction through the walls of the humidification component.

The all-polymer construction eliminates the need for an expensive conductive metallic base (e.g. aluminum), greatly simplifying the construction and lowering the cost. The humidification component of the present technology is, in one embodiment, producible by a blow molding process, which produces a single part design with no multi-part joints/seals. As described herein, multi-part joints/seals are susceptible to failures. The volume of the water may alternatively be heated by a combination of conduction and radiation heating (e.g. IR). Examples of materials that may be used for the humidification component are, but not limited to, the following: polyphenylene sulfide; cross-linked polyethylene; polysulfone; polycarbonate; and a conductive polymer.

Figure 12:
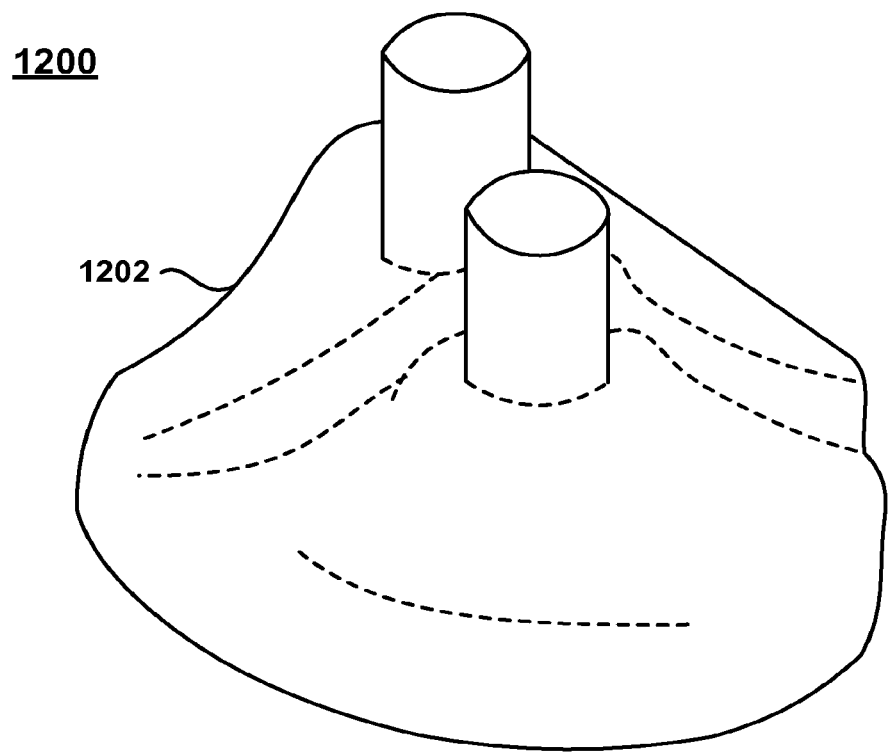
FIG. 12 shows an apparatus, in accordance with embodiments of the present technology.

FIG. 12 shows an apparatus 1200, including a humidification component 1202, according to embodiments of the present technology. Referring now to FIGS. 1 and 12, the humidification component 1202 holds a water volume 104 and is entirely comprised of a non-metallic material. The non-metallic material conducts heat, which is received from a heating element 110, to the water volume 104. The non-metallic material, in one embodiment, may be but is not limited to the following: an all-polymer material; glass; and fabric having some conductive properties. Of note, the humidification component 1202 of FIG. 12, in one embodiment, is the humidification component 102 of FIG. 1. The discussion of the humidification component 1202 herein is based on its relation to other components shown in FIG. 1 and as is discussed herein with reference to FIG. 1.

In one embodiment, the humidification component 1202 is in contact with the heating element 110 while it is receiving heat. For example, in one embodiment, the heating element 110 is a hot plate. The humidification component 1202 is positioned adjacent to the hot plate, in one embodiment. In one embodiment, the humidification component 1202 and the heating element 110 are independent of each other.

In another embodiment, the humidification component 1202 is comprised entirely of a polymer material, such as, but not limited to, the following material: cross-linked polyethylene; polyphenylene sulfide; polysulfone; polycarbonate; and a conductive polymer. However, since in one embodiment, the humidification component 1202 is constructed entirely of an all-polymer material and the humidification component 1202 has a high melting point and a sufficiently high glass transition temperature or heat deflection temperature, the humidification component 1202 does not soften or degrade during typical heating by a heating element 110.

In another embodiment, the humidification component 1202 transfers the heat received from the heating element 110 to the water volume 104 through radiation heating (e.g. IR). For example, a heating element 110 may provide IR energy emission, which the non-metallic material of the humidification component 1202 transfers to the water volume 104. In yet another embodiment, the water volume 104 is heated by a combination of conduction and radiation heating.

In one embodiment, the humidification component 1202 is injection molded. The process of injection molding enables the humidification component 1202 to be of a single piece construction. The single piece construction provides for a much lower manufacturing cost and a simplified humidification component design, as is already described herein. In another embodiment, the humidification component 1202 is injection molded. The process of injection molding the humidification component 1202 may involve more than one piece and/or more than one material which is welded or bonded together to become a single piece. Thus, the humidification component 1202, constructed entirely of a non-metallic material, may include two or more pieces of material.

Thus, embodiments of the present technology provide an apparatus that utilizes a simple humidification component constructed entirely of a non-metallic material, which is capable of conducting heat through its base and/or walls to the volume of water residing within the humidification component.

FIG. 13 is a flow diagram of a method 1300 for providing humidification in a respiratory system, according to an embodiment of the present technology. Referring to FIGS. 1, 12 and 13, at 1302 and as described herein, method 1300 includes receiving, at a humidification component 1202, heat from a heating element 110. The humidification component 1202 holds a water volume 104 and is entirely constructed of a non-metallic material. In one embodiment and as described herein, the humidification component 1202 and the heating element 110 are independent of each other. In other words, the humidification component 1202 and the heating element 110 are not in contact with each other. Yet, in another embodiment, the humidification component 1302 and the heating element 110 are in contact with each other. Moreover, in one embodiment, the heat that is received at the humidification component 1202 is transferred, by conduction, through at least one wall of the humidification component 1202 to the water volume 104.

Thus, embodiments of the present technology provide a respiratory humidification method which utilizes a simple humidification component constructed of a non-metallic material which conducts heat through its base and/or walls to a water volume held within.

Section 5: Automatically Setting a Humidification Level

Patients whose upper airways have been bypassed by either a tracheostomy or endotracheal tube need a higher level of humidity during respiratory therapy. Patients whose natural humidification system (i.e. upper airways) has not been bypassed need a lower level of humidity during respiratory therapy. These two conditions are commonly referred to in the industry as "invasive mode" and "non-invasive mode". In other words, in general, the invasive mode is the condition in which the upper airways are bypassed. The non-invasive mode is the condition in which the upper airways are not bypassed. Presently, a caregiver is required to determine and manually select the correct mode on the humidification system.

Further, the flow patterns associated with different respiratory therapies are distinct and are able to be categorized. For example, as a generality, the cyclical flow rates of a patient breathing with his upper airways will have a unique flow pattern. Similarly, most non-invasive flow rates that have a steady flow rate or less extreme flow rate changes will also have a unique flow pattern. Other therapies such as high flow therapies also have unique flow characteristics.

Embodiments of the present technology simplify the setup of the humidification system by automatically determining the appropriate mode of respiratory therapy and the related humidification level setting needed for the patient during the respiratory therapy. The appropriate mode and hence the related humidification level setting depends on the respiratory therapy situation.

The following is a description of five differing situational examples, showing the variation in respiratory therapy situations requiring a specific humidification level setting.

Situation One: Sick infants often require intubation and respiratory support within the perinatal period. These patients are typically ventilated using gas delivery systems that provide a relatively constant flow of gas at the machine outlet, at a rate, for example, of between 4 and 8 liters/minute. Pressure variation is imposed through use of a controlled valve in the exhalation gas conduit, and exhalation breathing circuit heater wires are employed. The cyclical variation in pressure will have a typical frequency in excess of 30 breaths/minute, with pressure changes that exceed, for example, 4 mbar amplitude. For these patients, the appropriate humidification level setting is a high humidity setting, such as, for example, 44 mgH$_2$O/liter of breathing gas.

Situation Two: Less sick infants may be provided with non-invasive respiratory support using a nasal cannula or a face mask. These patients are typically ventilated using gas delivery systems that provide a relatively constant flow of gas at the machine outlet, at a rate of no more than, for example, 10 liters/minute. However, in this population, pressure in the breathing circuit is relatively constant, with cyclical changes that are less than the threshold of, for example, 4 mbar. For these patients, the appropriate humidification level setting is a lower humidity setting.

Situation Three: Acutely sick older children or adults may be provided with invasive respiratory support using an endotracheal tube or tracheostomy. These patients are typically ventilated using gas delivery systems that provide a non-continuous flow of gas at the machine outlet. During patient exhalation, there is a minimal rate of flow of no more than, for example, 5 liters/minute. During patient inhalation, flow is increased, often with a peak value in excess of, for example, 20 liters/minute, and a decreasing flow waveform. For these patients, the appropriate humidification level setting is a high humidity setting of, for example, 44 mgH$_2$O/liter of breathing gas.

Situation Four: Chronically sick older children or adults may be provided with non-invasive respiratory support using a single breathing circuit tube that conveys gas to the patient, and a mouth or face mask that incorporates an orifice for egress of exhaled gas. The exhalation tube is absent and this can be identified by the humidification component as the absence of expiratory tube heating wires. These patients are typically ventilated using gas delivery systems that provide a non-continuous flow of gas at the machine outlet, but such that the pressure and flow have a characteristic correlation. During patient exhalation, there is a lower rate of flow which is determined by the level of positive pressure support required and the characteristic of the mask orifice, for example, 15 liters/minute at a pressure level of 3 mbar. During patient inhalation, there is a higher but relatively constant rate of flow, for example, 45 liters/minute at a pressure level of 20 mbar. For these patients, the appropriate humidification level setting is a lower humidity setting.

Situation Five: Less acutely sick patients may be provided with non-invasive respiratory support using a "High Flow" apparatus. This provides a constant flow of breathing gas through a cannula that is inserted into the patient's nasopharynx, in order to flush exhaled carbon dioxide from the nasopharynx, introduce oxygen into this space, and thereby reduce the effort required by the patient to achieve adequate gas exchange. In this configuration, the flow of gas is at a constant rate, which may be anywhere within a range of, for example, 2 to 60 liters/minute. In this configuration, the pressure of the air in the breathing circuit does not show cyclical variation. For these patients, the appropriate humidification level setting is a lower humidity setting.

Figure 14A:
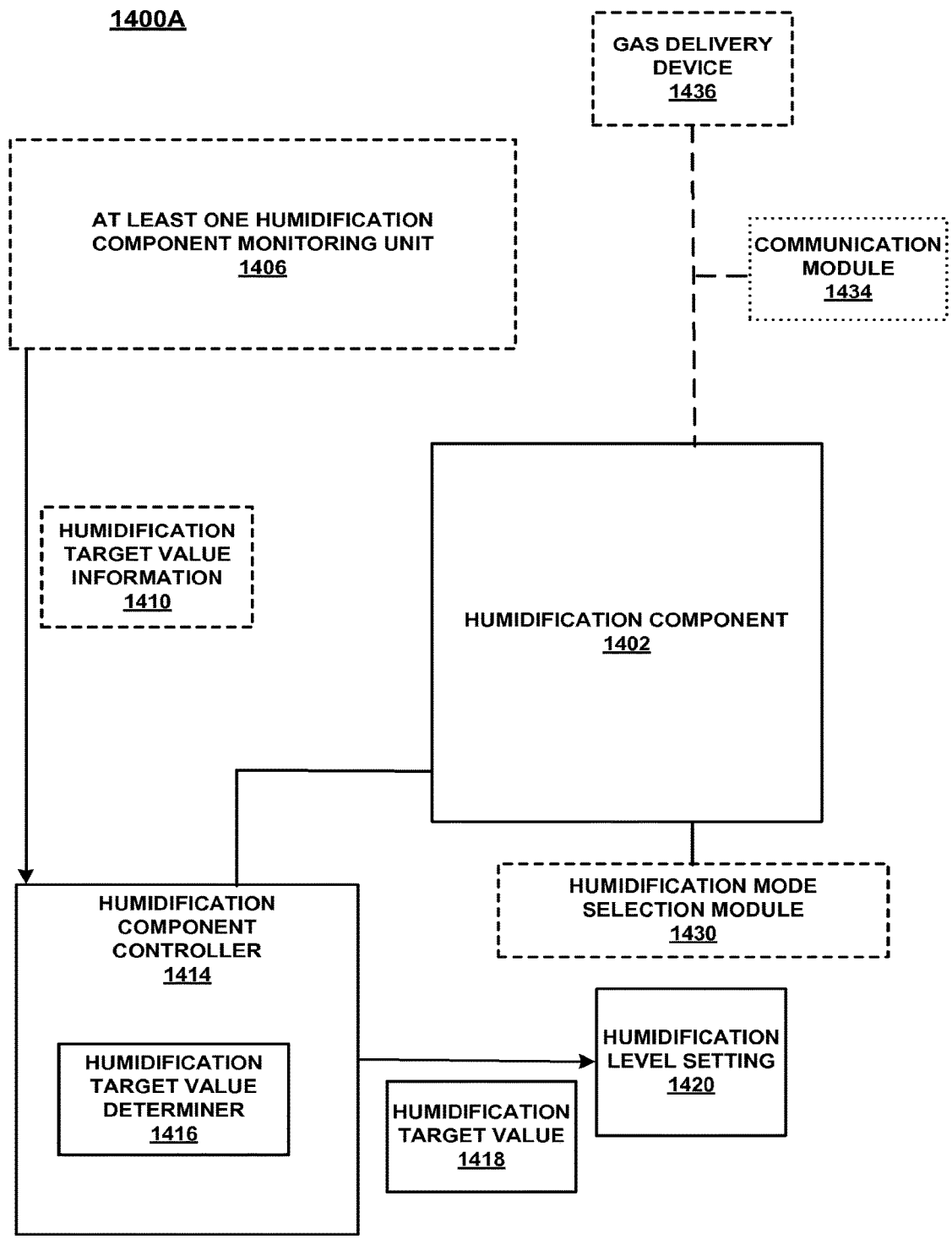
FIG. 14A shows a system for providing humidification to gas to be provided to a patient to support breathing, in accordance with embodiments of the present technology.

FIG. 14A shows a system 1400A for providing humidification to gas to be provided to a patient to support breathing, according to embodiments of the present technology. Referring now to FIG. 14A, the system 1400A includes a humidification component 1402 that adds water vapor to the gas that is provided to a patient to support breathing through a breathing circuit tubing and a humidification component controller 1414 that is coupled with the humidification component 1402 and receives humidification target value information 1410. In one embodiment, the humidification component controller 1414 includes a humidification target value determiner 1416. The humidification target value determiner 1416 determines, based on the received humidification target value information 1410, a humidification target value 1418 of at least two possible humidification target values. The humidification target value 1418 identifies a humidification level setting 1420 that corresponds to the patient.

In one embodiment, the humidification component 1402 is a humidification chamber as is common in the art. However, it should be appreciated that the humidification component 1402 may be any structure capable of adding water vapor to gas and operating with the other components described herein to achieve the functions described herein.

In one embodiment, the humidification target value information 1410 may be, but is not limited to, one or more of the following: a pattern of breathing of the patient; a gas flow rate; a geometry of a portion (a whole or less than a whole) of the breathing circuit tubing; a radio frequency identification (RFI) of the breathing circuit tubing; a wire resistance of a portion (a whole or less than a whole) of the breathing circuit tubing; tube heater wire information; and a determined pressure comprising a pressure relative to atmospheric pressure of the gas in the breathing circuit tubing.

In one embodiment, the gas flow rate refers to the flow rate of the gas through the patient breathing circuiting tubing, including the average flow rate. In another embodiment, the tube heater wire information includes at least one of a presence and an absence of a tube heater wire being coupled with the patient breathing tube. The tube heater wire information may also include information such as, but is not limited to, the following: heater wire resistance; RFID tags; and unique connector geometries which identify the breathing circuit tubing for patient size or therapy type.

In one embodiment, the system 1400A further includes at least one humidification component monitoring unit 1406 that is coupled with the humidification component 1402 and determines the humidification target value information 1410. For example, the at least one humidification component monitoring unit 1406 may be, but is not limited to, one or more of the following: a gas flow rate determiner that characterizes a rate of a flow of the gas to the breathing circuit tubing, thereby achieving a characterized rate of gas flow; a breathing circuit tubing configuration information detector that determines breathing circuit tubing configuration information; a tube heater wire detector that detects the tube heater wire information as is described herein; a pressure sensor that detects a pressure relative to atmospheric pressure of the gas in the breathing circuit tubing, thereby achieving a determined pressure; and an optical sensing module that optically senses humidification target value information 1410.

In one embodiment, the gas flow rate determiner is positioned within the humidification component 1402 and/or at the entrance to the patient breathing tube. It should be appreciated that the gas flow rate determiner may be any flow sensing technology, such as but not limited to the following: pressure differential readings; hot wire technology; and hot thermistor technology. In some embodiments, flow measurements may even be provided from another device, such as but not limited to, a flow generator, a flow blower, or a flow ventilator. In one embodiment, if the gas flow rate determiner is unable to determine the pattern of breathing, then the system 1400A defaults to a predetermined humidity level setting. In one embodiment, the predetermined humidity level setting is that setting that is determined to be a safe humidity level for the patient.

In one instance, the breathing circuit tubing configuration information determiner detects the breathing circuit tubing configuration information through sensors designed to detect such information. In another instance, the breathing circuit tubing configuration information determiner receives the breathing circuit tubing configuration information from another component. As described herein, the breathing circuit tubing configuration information, includes, but is not limited to, the following: a geometry of a portion of the breathing circuit tubing; a RFI of the breathing circuit tubing; and a wire resistance of a portion of the breathing circuit tubing. For example, the breathing circuit tubing configuration information detector detects the geometry of a connector (in one example, a disposable component of the breathing circuit tubing) to distinguish the breathing circuit tubing for information such as, but not limited to, patient size (as discussed herein).

Further, in one embodiment, the optical sensing module may be, but is not limited to such, one of the following: an on-board bar code reader; and an optical color reader.

Further, in one embodiment, the humidification component controller 1414 includes a breathing circuit tubing size determiner. The breathing circuit tubing size determiner determines a size of the gas conduit based on the breathing circuit tubing configuration information.

Figure 14B:
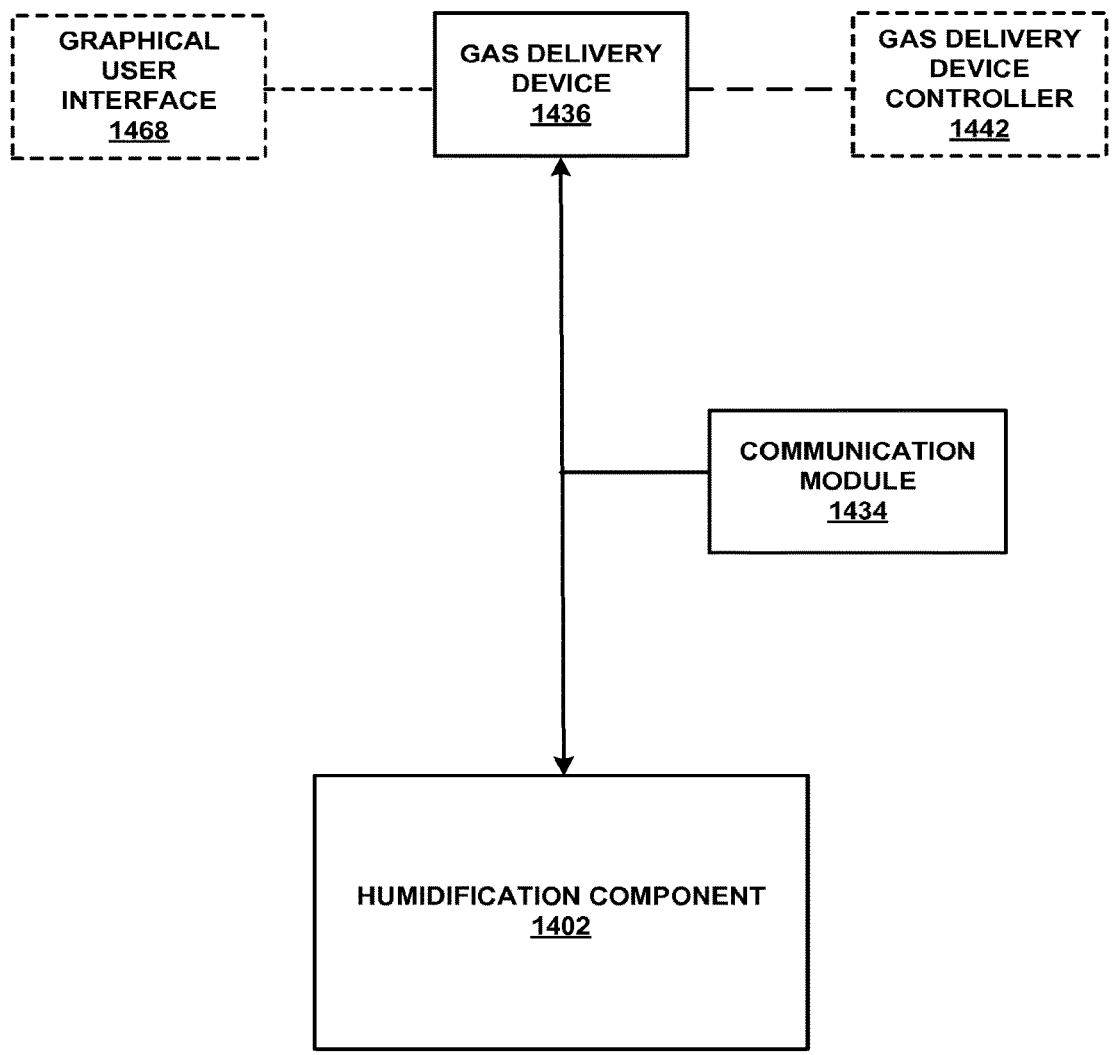
FIG. 14B shows a system for providing humidification to gas to be provided to a patient to support breathing, in accordance with embodiments of the present technology.

With reference now to FIGS. 7 and 14A and 14B (as will be discussed below), portions of the technology relating to the systems 1400A and 1400B are composed of computer-readable and computer-executable instructions that reside, for example, in computer-readable storage media of a computer system. That is, FIG. 7 illustrates one example of a type of computer that can be used to implement embodiments, which are discussed herein, of the present technology.

As discussed herein, FIG. 7 illustrates a computing system 700 used in accordance with embodiments of the present technology. In one embodiment, the computing system 700 and/or a portion thereof is the same as at least portions of the following (shown in FIGS. 14A and 14B): the humidification component controller 1414; the at least one humidification component monitoring unit 1406; the gas flow rate determiner; the humidification mode selection module 1430; the gas delivery device controller 1442 (of FIG. 14B); and the communication module 1434 (of FIG. 14B).

As described herein, the humidification component controller 1414 receives humidification target value information 1410 and includes a humidification target value determiner 1416. The humidification target value determiner 1416 determines, based on the received humidification target value information 1410, a humidification target value 1418. The humidification target value 1418 is one of at least two possible humidification target values, and identifies a humidification level setting 1420 corresponding to the patient.

In other words, once the humidification target value 1418 is selected, within this selection is the knowledge of the humidification level setting 1420 that the patient needs, based on the received humidification target value information 1410. The two possible humidification target values are humidification target values that are stored within a storage module of the humidification component controller 1414 and are available for selection, once the humidification target value information 1410 is received.

In one embodiment, the system 1400A further includes a humidification mode selection module 1430 that is coupled with the humidification component 1402. The humidification mode selection module 1430 communicates the humidification level setting 1420 to an operator 1432 of the system 1400A as being "selected". The method of communication may be via wire and/or wirelessly. In one embodiment, the operator 1432 is a human controlling a portion of the system. The portion of the system may be the whole system or a part less than the whole system.

In one embodiment, the system 1400A includes a gas delivery device 1436 that is coupled with the humidification component 1402. The gas delivery device 1436 controls a delivery of the gas to the humidification component 1402. In one embodiment, the gas delivery device 1436 may be a lung ventilator. Of note, the gas delivery device 1436 may be any device that is able to deliver gas to the humidification component 1402, as described herein. Further, the gas delivery device 1436, in one embodiment, provides measurements, such as but not limited to, a determined pressure and/or pattern of breathing information. In one embodiment, these measurements are gathered from the at least one humidification component monitoring unit 1406 with which the gas delivery device 1436 is coupled.

In one embodiment, the system 1400A includes a communication module 1434 that is coupled with the gas delivery device 1436 and the humidification component 1402. The communication module 1434 communicates information between the gas delivery device 1436 and the humidification component 1402. The coupling of the communication module 1434 with the gas delivery device 1436 and the humidification component 1402 may be, but is not limited to, a cable, cables, or a wireless communications interface such as a Bluetooth, a Zigbee, a WiFi or other data communications technology. The information includes the humidification target value information 1410. Of note, in this embodiment, the gas delivery device 1436 is coupled with the humidification component 1402 and the at least one humidification component monitoring unit 1406, wherein the gas delivery device 1436 controls a delivery of the gas to the humidification component 1402.

Referring now to FIG. 14B, a system 1400B is shown for providing humidification to gas to be provided to a patient to support breathing, according to one embodiment of the present technology. System 1400B includes a humidification component 1402 that adds water vapor to the gas, a gas delivery device 1436 coupled with the humidification component 1402 and that controls a delivery of the gas to the humidification component, and a communication module 1434 that is coupled with the gas delivery device 1436 and the humidification component 1402. The communication module 1434, in one embodiment, communicates humidification target value information 1410 between the humidification component 1402 and the gas delivery device 1436. The humidification component 1410 and the gas delivery device 1436 determine, based on the humidification target value information 1410, target operational information of the system 1400B associated with the patient.

In one embodiment, the system 1400B includes a gas delivery device controller 1442 that is coupled with the humidification component 1402 and stores the humidification target value information 1410. In one embodiment, the gas delivery device controller 1442 resides within the gas delivery device 1436. Yet, in another embodiment, the gas delivery device controller 1442 is wire and/or wirelessly attached to the gas delivery device 1436. In one embodiment, the gas delivery device controller 1442 includes an information store that stores the information, such as, but not limited to, the humidification target value information 1410.

In one embodiment and as described herein, the humidification target value information 1410 includes, but is not limited to, the following: a pattern of breathing of the patient; a geometry of a portion of the breathing circuit tubing; an RFI of the breathing circuit tubing; and a wire resistance of a portion of the breathing circuit tubing; tube heater wire information; a determined pressure including a pressure relative to atmospheric pressure of the gas in the breathing circuit tubing; and an operating parameter. In one embodiment, the operating parameter includes, but is not limited to, one or more of the following: a patient size; a clinical indication; and a respiratory support modality.

In one embodiment, the target operational information includes, but is not limited to, one or more of the following: a humidification level setting corresponding to the patient; an operational capability of the system 1400B; and an operation limit of the system 1400B.

In one embodiment, the system 1400B further includes a graphical user interface (GUI) 1468 that is coupled with the gas delivery device 1436. The GUI 1468 enables an operator of the system 1400B to communicate with the humidification component 1402. Additionally, in one embodiment, the GUI 1468 enables the operator to communicate with a portion of the system 1400B. It should be appreciated that a portion of the system may be the whole system 1400B (and any components within) or a part less than the whole of the system 1400B.

In one embodiment, the system 1400D includes an alarm 1470 that is coupled with the gas delivery device 1436. The alarm 1470 communicates a signal, wherein the signal indicates that a threshold level associated with an operation of the humidification component 1402 has been reached. For example, but not limited to such, a threshold level may be a predetermined level of humidity. When that particular level of humidity is detected, an alarm sounds. In another embodiment, the signal communicated is a message displayed on the GUI 1468. Of note, it should be understood that the signal may be indication that may be communicated via wire or wirelessly.

In one embodiment, the same graphical user interface may be used to communicate with the gas delivery device 1436 and the humidification component 1402, and control all devices coupled with such. While sharing a graphical user interface (and user input module coupled with the graphical user interface), the humidification component 1402 may be positioned below the gas delivery device 1436. This positioning facilitates an improved operator workflow and reduces the incidence of hazards associated with water spillage from the humidification component 1402 and components attached thereto.

Section 6: Further Embodiments

The following description of further embodiments references FIGS. 1-15D.

In one embodiment, a device for humidifying respiratory gases includes: a humidification component 402 configured for holding a water volume 404; a heating element 110 configured for converting received electrical energy to electromagnetic radiation, wherein the electromagnetic radiation is transferred to the water volume 404, thereby heating the water volume 404 to achieve a heated water volume; and at least one sensor 410 positioned external to the humidification component 402 and coupled with a control module, the at least one sensor 410 configured for sensing water related information in the humidification component 402 and providing the water related information to the control module 420, the water related information comprising data configured for being used to control an operation of a water level control element.

In one embodiment, a device for humidifying respiratory gases includes: a humidification component 402 configured for holding a water volume 404; a heating element 110 configured for converting received electrical energy to electromagnetic radiation, wherein the electromagnetic radiation is transferred to the water volume, thereby heating the water volume 404 to achieve a heated water volume; and at least one groove 904 disposed on a heater wire 802 of the device, the heater wire 802 being positioned in a respiratory gas conduit 810.

In one embodiment, a device for humidifying respiratory gases includes: a humidification component 402 configured for holding a water volume 404; and a heating element 110 configured for converting received electrical energy to electromagnetic radiation, wherein the electromagnetic radiation is transferred to the water volume 404, thereby heating the water volume 404 to achieve a heated water volume, wherein the humidification component 402 is comprised entirely of a non-metallic material, the non-metallic material configured for conducting heat to the water volume 404, the heat being received from a heating element 110.

In one embodiment, a device for humidifying respiratory gases includes: a humidification component 1402 configured for holding a water volume and for adding water vapor to a gas that is to be provided to a patient to support breathing; a heating element configured for converting received electrical energy to electromagnetic radiation, wherein the electromagnetic radiation is transferred to the water volume, thereby heating the water volume to achieve a heated water volume; and a humidification component controller 1414 coupled with the humidification component 1402 and configured for receiving the humidification target value information 1410, the humidification component controller 1414 including: a humidification target value determiner 1416 configured for determining, based on received humidification target value information 1410, a humidification target value 1418 of at least two possible humidification target values, the humidification target value 1418 identifying a humidification level setting 1420 corresponding to the patient.

In one embodiment, a device for humidifying respiratory gases includes: a humidification component 1402 configured for holding a water volume 404; a heating element 110 configured for converting received electrical energy to electromagnetic radiation, wherein the electromagnetic radiation is transferred to the water volume 404, thereby heating the water volume 404 to achieve a heated water volume; a respiratory gas conduit 810 comprising an input end 806 and an output end 804, the respiratory gas conduit 810 configured for receiving a gas 808 at the input end 806 and configured to transport the gas 808 to the output end 804; and a heater wire 802 disposed inside the respiratory gas conduit 810, the heater wire 802 including: a sheathing; and at least one groove 904 disposed on the sheathing, the at least one groove 904 configured for wicking up water from a region of condensation within the respiratory gas conduit 810 and transporting wicked up water to a re-evaporation region.

In one embodiment, a device for humidifying respiratory gases includes: a humidification component 1402 configured for holding a water volume 404 and for adding water vapor to a gas to be provided to a patient to support breathing; a heating element 110 configured for converting received electrical energy to electromagnetic radiation, wherein the electromagnetic radiation is transferred to the water volume 404, thereby heating the water volume 404 to achieve a heated water volume; a gas delivery device 1436 coupled with the humidification component 1402, the gas delivery device 1436 configured for controlling a delivery of the gas to the humidification component 1402; and a communication module 1434 coupled with the gas delivery device 1436 and the humidification component 1402, the communication module 1434 configured for communicating the humidification target value information 1410 between the gas delivery device controller 1442 and the humidification component 1402, the humidification component 1402 and the gas delivery device 1436 configured for determining, based on the humidification target value information, target operational information of a system associated with the patient, the system including the device.

In one embodiment, a device for humidifying respiratory gases includes: a humidification component 1402 configured for holding a water volume 404; a heating element 110 configured for converting received electrical energy to electromagnetic radiation, wherein the electromagnetic radiation is transferred to the water volume 404, thereby heating the water volume 404 to achieve a heated water volume; at least one sensor 410 positioned external to a humidification component 1402 and coupled with a control module 420, the at least one sensor 410 configured for sensing water related information in the humidification component 1402 and providing the water related information to the control module 420, the water related information comprising data configured for being used to control an operation of a water level control element; and at least one groove 904 disposed on a heater wire 802 of the device, the heater wire 802 being positioned in a respiratory gas conduit 810.

In one embodiment, a device for humidifying respiratory gases includes a humidification component 1402 configured for holding a water volume 404; a heating element 110 configured for converting received electrical energy to electromagnetic radiation, wherein the electromagnetic radiation is transferred to the water volume 404, thereby heating the water volume 404 to achieve a heated water volume; and at least one sensor 410 positioned external to the humidification component 1402 and coupled with a control module 420, the at least one sensor 410 configured for sensing water related information in the humidification component 1402 and providing the water related information to the control module 420, the water related information comprising data configured for being used to control an operation of a water level control element, wherein the humidification component 1402 is comprised entirely of a non-metallic material, the non-metallic material configured for conducting heat to the water volume 404, the heat being received from a heating element 110.

In one embodiment, a device for humidifying respiratory gases includes: a humidification component 1402 configured for holding a water volume 404 and for adding water vapor to a gas to be provided to a patient to support breathing; a heating element 110 configured for converting received electrical energy to electromagnetic radiation, wherein the electromagnetic radiation is transferred to the water volume 404, thereby heating the water volume 404 to achieve a heated water volume; at least one sensor 410 positioned external to the humidification component 1402 and coupled with a control module 420, the at least one sensor 410 configured for sensing water related information in the humidification component 1402 and providing the water related information to the control module 420, the water related information comprising data configured for being used to control an operation of a water level control element; and a humidification component controller 1414 coupled with the humidification component 1402 and configured for receiving the humidification target value information 1410, the humidification component controller 1414 including: a humidification target value determiner 1416 configured for determining, based on received humidification target value information 1410, a humidification target value 1418 of at least two possible humidification target values, the humidification target value 1418 identifying a humidification level setting 1420 corresponding to the patient.

In one embodiment, a device for humidifying respiratory gases includes a humidification component 1402 configured for holding a water volume 404; a heating element 110 configured for converting received electrical energy to electromagnetic radiation, wherein the electromagnetic radiation is transferred to the water volume 404, thereby heating the water volume 404 to achieve a heated water volume; at least one sensor 410 positioned external to the humidification component 1402 and coupled with a control module 420, the at least one sensor 410 configured for sensing water related information in the humidification component 1402 and providing the water related information to the control module 420, the water related information comprising data configured for being used to control an operation of a water level control element; a respiratory gas conduit 810 comprising an input end 806 and an output end 804, the respiratory gas conduit 810 configured for receiving gas at the input end 806 and configured to transport the gas 808 to the output end 804; and a heater wire 802 disposed inside the respiratory gas conduit 810, the heater wire 802 including: a sheathing; and at least one groove 904 disposed on the sheathing, the at least one groove 904 configured for wicking up water from a region of condensation within the respiratory gas conduit 810 and transporting wicked up water to a re-evaporation region.

In one embodiment, a device for humidifying respiratory gases includes: a humidification component 1402 configured for holding a water volume 404 and for adding water vapor to a gas to be provided to a patient to support breathing; a heating element 110 configured for converting received electrical energy to electromagnetic radiation, wherein the electromagnetic radiation is transferred to the water volume 404, thereby heating the water volume 404 to achieve a heated water volume; at least one sensor 410 positioned external to a humidification component 1402 and coupled with a control module 420, the at least one sensor 410 configured for sensing water related information in the humidification component 1402 and providing the water related information to the control module 420, the water related information including data configured for being used to control an operation of a water level control element; a gas delivery device 1436 coupled with the humidification component 1402, the gas delivery device 1436 configured for controlling a delivery of the gas to the humidification component 1402; and a communication module 1434 coupled with the gas delivery device 1436 and the humidification component 1402, the communication module 1434 configured for communicating the humidification target value information 1410 between the gas delivery device controller 1442 and the humidification component 1402, the humidification component 1402 and the gas delivery device 1436 configured for determining, based on the humidification target value information, target operational information of the system associated with the patient, the system including the device.

In one embodiment, a device for humidifying respiratory gases includes: a humidification component 1402 configured for holding a water volume 404; a heating element 110 configured for converting received electrical energy to electromagnetic radiation, wherein the electromagnetic radiation is transferred to the water volume 404, thereby heating the water volume 404 to achieve a heated water volume; and at least one groove 904 disposed on a heater wire 802 of the device, the heater wire 802 being positioned in a respiratory gas conduit 810, wherein the humidification component 1402 is comprised entirely of a non-metallic material, the non-metallic material configured for conducting heat to the water volume 404, the heat being received from a heating element 110.

In one embodiment, a device for humidifying respiratory gases includes: a humidification component 1402 configured for holding a water volume 404 and for adding water vapor to a gas to be provided to a patient to support breathing; a heating element 110 configured for converting received electrical energy to electromagnetic radiation, wherein the electromagnetic radiation is transferred to the water volume 404, thereby heating the water volume 404 to achieve a heated water volume; at least one groove 904 disposed on a heater wire 802 of the device, the heater wire 802 being positioned in a respiratory gas conduit 810; and a humidification component controller 1414 coupled with the humidification component 1402 and configured for receiving the humidification target value 1418 information 1410, the humidification component controller 1414 including: a humidification target value determiner 1416 configured for determining, based on received humidification target value information 1410, a humidification target value 1418 of at least two possible humidification target values, the humidification target value 1418 identifying a humidification level setting 1420 corresponding to the patient.

In one embodiment, a device for humidifying respiratory gases includes: a humidification component 1402 configured for holding a water volume 404; a heating element 110 configured for converting received electrical energy to electromagnetic radiation, wherein the electromagnetic radiation is transferred to the water volume 404, thereby heating the water volume 404 to achieve a heated water volume 404; at least one groove 904 disposed on a heater wire 802 of the device, the heater wire 802 being positioned in a respiratory gas conduit 810; a respiratory gas conduit 810 including an input end 806 and an output end 804, the respiratory gas conduit 810 configured for receiving gas at the input end 806 and configured to transport the gas to the output end 804; and a heater wire 802 disposed inside the respiratory gas conduit 810, the heater wire 802 including: a sheathing; and at least one groove 904 disposed on the sheathing, the at least one groove 904 configured for wicking up water from a region of condensation within the respiratory gas conduit 810 and transporting wicked up water to a re-evaporation region.

In one embodiment, a device for humidifying respiratory gases includes: a humidification component 1402 configured for holding a water volume 404 and for adding water vapor to a gas to be provided to a patient to support breathing; a heating element 110 configured for converting received electrical energy to electromagnetic radiation, wherein the electromagnetic radiation is transferred to the water volume 404, thereby heating the water volume 404 to achieve a heated water volume 404; at least one groove 904 disposed on a heater wire 802 of the device, the heater wire 802 being positioned in a respiratory gas conduit 810; a gas delivery device 1436 coupled with the humidification component 1402, the gas delivery device 1436 configured for controlling a delivery of the gas to the humidification component 1402; and a communication module 1434 coupled with the gas delivery device 1436 and the humidification component 1402, the communication module 1434 configured for communicating the humidification target value information 1410 between the gas delivery device controller 1442 and the humidification component 1402, the humidification component 1402 and the gas delivery device 1436 configured for determining, based on the humidification target value information, target operational information of a system associated with the patient, the system including the device.

A device for humidifying respiratory gases, the device including: a humidification component 1402 configured for holding a water volume 404 and for adding water vapor to a gas to be provided to a patient to support breathing; a heating element 110 configured for converting received electrical energy to electromagnetic radiation, wherein the electromagnetic radiation is transferred to the water volume 404, thereby heating the water volume 404 to achieve a heated water volume 404, wherein the humidification component 1402 is comprised entirely of a non-metallic material, the non-metallic material configured for conducting heat to the water volume 404, the heat being received from a heating element 110; and a humidification component controller 1414 coupled with the humidification component 1402 and configured for receiving the humidification target value 1418 information 1410, the humidification component controller 1414 including: a humidification target value 1418 determiner 1416 configured for determining, based on received humidification target value 1418 information 1410, a humidification target value 1418 of at least two possible humidification target values 1418, the humidification target value 1418 identifying a humidification level setting 1420 corresponding to the patient.

In one embodiment, a device for humidifying respiratory gases includes: a humidification component 1402 configured for holding a water volume 404; a heating element 110 configured for converting received electrical energy to electromagnetic radiation, wherein the electromagnetic radiation is transferred to the water volume 404, thereby heating the water volume 404 to achieve a heated water volume 404, wherein the humidification component 1402 is comprised entirely of a non-metallic material, the non-metallic material configured for conducting heat to the water volume 404, the heat being received from a heating element 110; a respiratory gas conduit 810 comprising an input end 806 and an output end 804, the respiratory gas conduit 810 configured for receiving gas at the input end 806 and configured to transport the gas to the output end 804; and a heater wire 802 disposed inside the respiratory gas conduit 810, the heater wire 802 including: a sheathing; and at least one groove 904 disposed on the sheathing, the at least one groove 904 configured for wicking up water from a region of condensation within the respiratory gas conduit 810 and transporting wicked up water to a re-evaporation region.

In one embodiment, a device for humidifying respiratory gases includes: a humidification component 1402 configured for holding a water volume 404 and for adding water vapor to a gas to be provided to a patient to support breathing; a heating element 110 configured for converting received electrical energy to electromagnetic radiation, wherein the electromagnetic radiation is transferred to the water volume 404, thereby heating the water volume 404 to achieve a heated water volume 404, wherein the humidification component 1402 is comprised entirely of a non-metallic material, the non-metallic material configured for conducting heat to the water volume 404, the heat being received from a heating element 110; a humidification component 1402 configured for adding water vapor to the gas; a gas delivery device 1436 coupled with the humidification component 1402, the gas delivery device 1436 configured for controlling a delivery of the gas to the humidification component 1402; and a communication module 1434 coupled with the gas delivery device 1436 and the humidification component 1402, the communication module 1434 configured for communicating the humidification target value information 1410 between the gas delivery device controller 1442 and the humidification component 1402, the humidification component 1402 and the gas delivery device 1436 configured for determining, based on the humidification target value information, target operational information of the system associated with the patient, the system including the device.

In one embodiment, a device for humidifying respiratory gases includes: a humidification component 1402 configured for holding a water volume 404 and for adding water vapor to a gas to be provided to a patient to support breathing; a heating element 110 configured for converting received electrical energy to electromagnetic radiation, wherein the electromagnetic radiation is transferred to the water volume 404, thereby heating the water volume 404 to achieve a heated water volume 404; a respiratory gas conduit 810 comprising an input end 806 and an output end 804, the respiratory gas conduit 810 configured for receiving gas at the input end 806 and configured to transport the gas to the output end 804; a heater wire 802 disposed inside the respiratory gas conduit 810, the heater wire 802 including: a sheathing; and at least one groove 904 disposed on the sheathing, the at least one groove 904 configured for wicking up water from a region of condensation within the respiratory gas conduit 810 and transporting wicked up water to a re-evaporation region; and a humidification component controller 1414 coupled with the humidification component 1402 and configured for receiving the humidification target value information 1410, the humidification component controller 1414 including: a humidification target value determiner 1416 configured for determining, based on received humidification target value information 1410, a humidification target value 1418 of at least two possible humidification target values, the humidification target value 1418 identifying a humidification level setting 1420 corresponding to the patient.

In one embodiment, a device for humidifying respiratory gases includes: a humidification component 1402 configured for holding a water volume 404 and for adding water vapor to a gas to be provided to a patient to support breathing; a heating element 110 configured for converting received electrical energy to electromagnetic radiation, wherein the electromagnetic radiation is transferred to the water volume 404, thereby heating the water volume 404 to achieve a heated water volume 404; a respiratory gas conduit 810 comprising an input end 806 and an output end 804, the respiratory gas conduit 810 configured for receiving gas at the input end 806 and configured to transport the gas to the output end 804; a heater wire 802 disposed inside the respiratory gas conduit 810, the heater wire 802 comprising: a sheathing; and at least one groove 904 disposed on the sheathing, the at least one groove 904 configured for wicking up water from a region of condensation within the respiratory gas conduit 810 and transporting wicked up water to a re-evaporation region; a gas delivery device 1436 coupled with the humidification component 1402, the gas delivery device 1436 configured for controlling a delivery of the gas to the humidification component 1402; and a communication module 1434 coupled with the gas delivery device 1436 and the humidification component 1402, the communication module 1434 configured for communicating the humidification target value information 1410 between the gas delivery device controller 1442 and the humidification component 1402, the humidification component 1402 and the gas delivery device 1436 configured for determining, based on the humidification target value information, target operational information of a system associated with the patient, wherein the system includes the device.

In one embodiment, a device for humidifying respiratory gases includes: a humidification component 1402 configured for holding a water volume 404; a heating element 110 configured for converting received electrical energy to electromagnetic radiation, wherein the electromagnetic radiation is transferred to the water volume 404, thereby heating the water volume 404 to achieve a heated water volume 404; at least one sensor 410 positioned external to a humidification component 1402 and coupled with a control module 420, the at least one sensor 410 configured for sensing water related information in the humidification component 1402 and providing the water related information to the control module 420, the water related information comprising data configured for being used to control an operation of a water level control element; and at least one groove 904 disposed on a heater wire 802 of the device, the heater wire 802 being positioned in a respiratory gas conduit 810, wherein the humidification component 1402 is comprised entirely of a non-metallic material, the non-metallic material configured for conducting heat to the water volume 404, the heat being received from a heating element 110.

In one embodiment, a device for humidifying respiratory gases includes: a humidification component 1402 configured for holding a water volume 404 and for adding water vapor to a gas to be provided to a patient to support breathing; a heating element 110 configured for converting received electrical energy to electromagnetic radiation, wherein the electromagnetic radiation is transferred to the water volume 404, thereby heating the water volume 404 to achieve a heated water volume 404; at least one sensor 410 positioned external to a humidification component 1402 and coupled with a control module 420, the at least one sensor 410 configured for sensing water related information in the humidification component 1402 and providing the water related information to the control module 420, the water related information comprising data configured for being used to control an operation of a water level control element; and a humidification component controller 1414 coupled with the humidification component 1402 and configured for receiving the humidification target value information 1410, the humidification component controller 1414 including: a humidification target value determiner 1416 configured for determining, based on received humidification target value information 1410, a humidification target value 1418 of at least two possible humidification target values, the humidification target value 1418 identifying a humidification level setting 1420 corresponding to the patient.

In one embodiment, a device for humidifying respiratory gases includes: a humidification component 1402 configured for holding a water volume 404 and adding water vapor to a gas to be provided to a patient to support breathing; a heating element 110 configured for converting received electrical energy to electromagnetic radiation, wherein the electromagnetic radiation is transferred to the water volume 404, thereby heating the water volume 404 to achieve a heated water volume 404; at least one sensor 410 positioned external to a humidification component 1402 and coupled with a control module 420, the at least one sensor 410 configured for sensing water related information in the humidification component 1402 and providing the water related information to the control module 420, the water related information comprising data configured for being used to control an operation of a water level control element; at least one groove 904 disposed on a heater wire 802 of the device, the heater wire 802 being positioned in a respiratory gas conduit 810; a gas delivery device 1436 coupled with the humidification component 1402, the gas delivery device 1436 configured for controlling a delivery of the gas to the humidification component 1402; and a communication module 1434 coupled with the gas delivery device 1436 and the humidification component 1402, the communication module 1434 configured for communicating the humidification target value information 1410 between the gas delivery device controller 1442 and the humidification component 1402, the humidification component 1402 and the gas delivery device 1436 configured for determining, based on the humidification target value information, target operational information of the system associated with the patient, the system including the device.

In one embodiment, a device for humidifying respiratory gases includes: a humidification component 1402 configured for holding a water volume 404 and for adding water vapor to a gas to be provided to a patient to support breathing; a heating element 110 configured for converting received electrical energy to electromagnetic radiation, wherein the electromagnetic radiation is transferred to the water volume 404, thereby heating the water volume 404 to achieve a heated water volume 404; at least one sensor 410 positioned external to a humidification component 1402 and coupled with a control module 420, the at least one sensor 410 configured for sensing water related information in the humidification component 1402 and providing the water related information to the control module 420, the water related information comprising data configured for being used to control an operation of a water level control element, wherein the humidification component 1402 is comprised entirely of a non-metallic material, the non-metallic material configured for conducting heat to the water volume 404, the heat being received from a heating element 110; and a humidification component controller 1414 coupled with the humidification component 1402 and configured for receiving the humidification target value information 1410, the humidification component controller 1414 including: a humidification target value determiner 1416 configured for determining, based on received humidification target value information 1410, a humidification target value 1418 of at least two possible humidification target values, the humidification target value 1418 identifying a humidification level setting 1420 corresponding to the patient.

In one embodiment, a device for maintaining a water level in a respiratory humidification system includes: at least one sensor 410 positioned external to a humidification component 1402 and coupled with a control module 420, the at least one sensor 410 configured for sensing water related information in the humidification component 1402 and providing the water related information to the control module 420, the water related information comprising data configured for being used to control an operation of a water level control element; and at least one groove 904 disposed on a heater wire 802 of the device, the heater wire 802 being positioned in a respiratory gas conduit 810.

In one embodiment, a device for maintaining a water level in a respiratory humidification system includes: at least one sensor 410 positioned external to a humidification component 1402 and coupled with a control module 420, the at least one sensor 410 configured for sensing water related information in the humidification component 1402 and providing the water related information to the control module 420, the water related information comprising data configured for being used to control an operation of a water level control element, wherein the humidification component 1402 is configured for holding a water volume 404, the humidification component 1402 comprised entirely of a non-metallic material, the non-metallic material configured for conducting heat to the water volume 404, the heat being received from a heating element 110.

In one embodiment, a device for maintaining a water level in a respiratory humidification system includes: at least one sensor 410 positioned external to a humidification component 1402 and coupled with a control module 420, the at least one sensor 410 configured for sensing water related information in the humidification component 1402 and providing the water related information to the control module 420, the water related information comprising data configured for being used to control an operation of a water level control element, wherein the humidification component 1402 is configured for adding water vapor to a gas to be provided to a patient to support breathing; and a humidification component controller 1414 coupled with the humidification component 1402 and configured for receiving the humidification target value information 1410, the humidification component controller 1414 including: a humidification target value determiner 1416 configured for determining, based on received humidification target value information 1410, a humidification target value 1418 of at least two possible humidification target values, the humidification target value 1418 identifying a humidification level setting 1420 corresponding to the patient.

In one embodiment, a device for maintaining a water level in a respiratory humidification system includes: at least one sensor 410 positioned external to a humidification component 1402 and coupled with a control module 420, the at least one sensor 410 configured for sensing water related information in the humidification component 1402 and providing the water related information to the control module 420, the water related information including data configured for being used to control an operation of a water level control element; a respiratory gas conduit 810 comprising an input end 806 and an output end 804, the respiratory gas conduit 810 configured for receiving gas at the input end 806 and configured to transport the gas to the output end 804; and a heater wire 802 disposed inside the respiratory gas conduit 810, the heater wire 802 including: a sheathing; and at least one groove 904 disposed on the sheathing, the at least one groove 904 configured for wicking up water from a region of condensation within the respiratory gas conduit 810 and transporting wicked up water to a re-evaporation region.

In one embodiment, a device for maintaining a water level in a respiratory humidification system includes: at least one sensor 410 positioned external to a humidification component 1402 and coupled with a control module 420, the at least one sensor 410 configured for sensing water related information in the humidification component 1402 and providing the water related information to the control module 420, the water related information comprising data configured for being used to control an operation of a water level control element, wherein the humidification component 1402 is configured for adding water vapor to a gas to be provided to a patient to support breathing; a gas delivery device 1436 coupled with the humidification component 1402, the gas delivery device 1436 configured for controlling a delivery of the gas to the humidification component 1402; and a communication module 1434 coupled with the gas delivery device 1436 and the humidification component 1402, the communication module 1434 configured for communicating the humidification target value information 1410 between the gas delivery device controller 1442 and the humidification component 1402, the humidification component 1402 and the gas delivery device 1436 configured for determining, based on the humidification target value information, target operational information of a system associated with the patient, wherein the system includes the device.

In one embodiment, a device for maintaining a water level in a respiratory humidification system includes: at least one sensor 410 positioned external to a humidification component 1402 and coupled with a control module 420, the at least one sensor 410 configured for sensing water related information in the humidification component 1402 and providing the water related information to the control module 420, the water related information comprising data configured for being used to control an operation of a water level control element; and at least one groove 904 disposed on a heater wire 802 of the device, the heater wire 802 being positioned in a respiratory gas conduit 810, wherein the humidification component 1402 is configured for holding a water volume 404, the humidification component 1402 comprised entirely of a non-metallic material, the non-metallic material configured for conducting heat to the water volume 404, the heat being received from a heating element 110.

In one embodiment, a device for maintaining a water level in a respiratory humidification system includes: at least one sensor 410 positioned external to a humidification component 1402 and coupled with a control module 420, the at least one sensor 410 configured for sensing water related information in the humidification component 1402 and providing the water related information to the control module 420, the water related information including data configured for being used to control an operation of a water level control element; at least one groove 904 disposed on a heater wire 802 of the device, the heater wire 802 being positioned in a respiratory gas conduit 810, wherein the humidification component 1402 is configured for holding a water volume 404 and for adding water vapor to a gas to be provided to a patient to support breathing; and a humidification component controller 1414 coupled with the humidification component 1402 and configured for receiving the humidification target value information 1410, the humidification component controller 1414 including: a humidification target value determiner 1416 configured for determining, based on received humidification target value information 1410, a humidification target value 1418 of at least two possible humidification target values, the humidification target value 1418 identifying a humidification level setting 1420 corresponding to the patient.

In one embodiment, a device for maintaining a water level in a respiratory humidification system includes: at least one sensor 410 positioned external to a humidification component 1402 and coupled with a control module 420, the at least one sensor 410 configured for sensing water related information in the humidification component 1402 and providing the water related information to the control module 420, the water related information comprising data configured for being used to control an operation of a water level control element; at least one groove 904 disposed on a heater wire 802 of the device, the heater wire 802 being positioned in a respiratory gas conduit 810, wherein the humidification component 1402 is configured for holding a water volume 404 and for adding water vapor to a gas to be provided to a patient to support breathing; a gas delivery device 1436 coupled with the humidification component 1402, the gas delivery device 1436 configured for controlling a delivery of the gas to the humidification component 1402; and a communication module 1434 coupled with the gas delivery device 1436 and the humidification component 1402, the communication module 1434 configured for communicating the humidification target value information 1410 between the gas delivery device controller 1442 and the humidification component 1402, the humidification component 1402 and the gas delivery device 1436 configured for determining, based on the humidification target value information 1410, target operational information of the system associated with the patient.

In one embodiment, a device for maintaining a water level in a respiratory humidification system includes: at least one sensor 410 positioned external to a humidification component 1402 and coupled with a control module 420, the at least one sensor 410 configured for sensing water related information in said humidification component 1402 and providing the water related information to the control module 420, the water related information comprising data configured for being used to control an operation of a water level control element, wherein the humidification component 1402 is configured for holding a water volume, the humidification component 1402 comprised entirely of a non-metallic material, the non-metallic material configured for conducting heat to the water volume, the heat being received from a heating element; at least one groove 904 disposed on a heater wire 802 of the device, the heater wire 802 being positioned in a respiratory gas conduit 810 coupled with the humidification component 1402; and a humidification component controller 1414 coupled with the humidification component 1402 and configured for receiving the humidification target value information 1410, the humidification component controller 1414 including: a humidification target value determiner 1416 configured for determining, based on received humidification target value information 1410, a humidification target value 1418 of at least two possible humidification target values, the humidification target value 1418 identifying a humidification level setting 1420 corresponding to the patient.

In one embodiment, a device for maintaining a water level in a respiratory humidification system includes: at least one sensor 410 positioned external to a humidification component 1402 and coupled with a control module 420, the at least one sensor 410 configured for sensing water related information in the humidification component 1402 and providing the water related information to the control module 420, the water related information comprising data configured for being used to control an operation of a water level control element, wherein the humidification component 1402 is configured for holding a water volume, the humidification component 1402 comprised entirely of a non-metallic material, the non-metallic material configured for conducting heat to the water volume, the heat being received from a heating element; at least one groove 904 disposed on a heater wire 802 of the device, the heater wire 802 being positioned in a respiratory gas conduit 810 coupled with the humidification component 1402; a gas delivery device 1436 coupled with the humidification component 1402, the gas delivery device 1436 configured for controlling a delivery of the gas to the humidification component 1402; and a communication module 1434 coupled with the gas delivery device 1436 and the humidification component 1402, the communication module 1434 configured for communicating humidification target value information between the humidification component 1402 and the gas delivery device 1436, the humidification component 1402 and the gas delivery device 1436 configured for determining, based on the humidification target value information 1410, target operational information of a system associated with the patient, wherein the system comprises the device.

In one embodiment, a system includes: a heater wire 802 that includes: at least one groove 904 disposed thereon, the heater wire 802 being positioned in a respiratory gas conduit 810; and a humidification component 1402 coupled with the heater wire 802, the humidification component 1402 configured for holding a water volume 404, the humidification component 1402 comprised entirely of a non-metallic material, the non-metallic material configured for conducting heat to the water volume 404, the heat being received from a heating element 110.

In one embodiment, a system including: a heater wire 802 includes: at least one groove 904 disposed thereon, the heater wire 802 being positioned in a respiratory gas conduit 810; a humidification component 1402 coupled with the heater wire 802, the humidification component 1402 configured for adding water vapor to the gas; and a humidification component controller 1414 coupled with the humidification component 1402 and configured for receiving the humidification target value information 1410, the humidification component controller 1414 including: a humidification target value determiner 1416 configured for determining, based on received humidification target value information 1410, a humidification target value 1418 of at least two possible humidification target values, the humidification target value 1418 identifying a humidification level setting 1420 corresponding to the patient.

In one embodiment, a system includes: a heater wire 802 that includes: at least one groove 904 disposed thereon, the heater wire 802 being positioned in a respiratory gas conduit 810; a humidification component 1402 coupled with the heater wire 802, the humidification component 1402 configured for adding water vapor to the gas; a gas delivery device 1436 coupled with the humidification component 1402, the gas delivery device 1436 configured for controlling a delivery of the gas to the humidification component 1402; and a communication module 1434 coupled with the gas delivery device 1436 and the humidification component 1402, the communication module 1434 configured for communicating the humidification target value information 1410 between the gas delivery device controller 1442 and the humidification component 1402, the humidification component 1402 and the gas delivery device 1436 configured for determining, based on the humidification target value information, target operational information of the system associated with the patient.

In one embodiment, a system including: a heater wire 802 that includes: at least one groove 904 disposed thereon, the heater wire 802 being positioned in a respiratory gas conduit 810; a humidification component 1402 coupled with said heater wire 802, the humidification component 1402 configured for holding a water volume 404 and for adding water vapor to a gas to be provided to a patient to support breathing, the humidification component 1402 comprised entirely of a non-metallic material, the non-metallic material configured for conducting heat to the water volume 404, the heat being received from a heating element 110; and a humidification component controller 1414 coupled with the humidification component 1402 and configured for receiving the humidification target value 1418 information 1410, the humidification component controller 1414 including: a humidification target value determiner 1416 configured for determining, based on received humidification target value information 1410, a humidification target value 1418 of at least two possible humidification target values, the humidification target value 1418 identifying a humidification level setting 1420 corresponding to the patient.

In one embodiment, a system includes a heater wire 802 including at least one groove 904 disposed thereon, the heater wire 802 being positioned in a respiratory gas conduit 810; a humidification component 1402 coupled with said heater wire 802, the humidification component 1402 configured for holding a water volume 404 and for adding water vapor to a gas to be provided to a patient to support breathing, the humidification component 1402 comprised entirely of a non-metallic material, the non-metallic material configured for conducting heat to the water volume 404, the heat being received from a heating element 110; a gas delivery device 1436 coupled with the humidification component 1402, the gas delivery device 1436 configured for controlling a delivery of the gas to the humidification component 1402; and a communication module 1434 coupled with the gas delivery device 1436 and the humidification component 1402, the communication module 1434 configured for communicating the humidification target value information 1410 between the gas delivery device controller 1442 and the humidification component 1402, the humidification component 1402 and the gas delivery device 1436 configured for determining, based on the humidification target value information, target operational information of the system associated with the patient.

In one embodiment, an apparatus includes: a humidification component 1402 configured for holding a water volume 404 and for adding water vapor to a gas to be provided to a patient to support breathing, the humidification component 1402 comprised entirely of a non-metallic material, the non-metallic material configured for conducting heat to the water volume 404, the heat being received from a heating element 110; and a humidification component controller 1414 coupled with the humidification component 1402 and configured for receiving the humidification target value information 1410, the humidification component controller 1414 including: a humidification target value determiner 1416 configured for determining, based on received humidification target value information 1410, a humidification target value 1418 of at least two possible humidification target values, the humidification target value 1418 identifying a humidification level setting 1420 corresponding to the patient.

In one embodiment, an apparatus includes: a humidification component 1402 configured for holding a water volume 404 and for adding water vapor to a gas to be provided to a patient to support breathing, the humidification component 1402 comprised entirely of a non-metallic material, the non-metallic material configured for conducting heat to the water volume 404, the heat being received from a heating element 110; a gas delivery device 1436 coupled with the humidification component 1402, the gas delivery device 1436 configured for controlling a delivery of the gas to the humidification component 1402; and a communication module 1434 coupled with the gas delivery device 1436 and the humidification component 1402, the communication module 1434 configured for communicating the humidification target value information 1410 between the gas delivery device controller 1442 and the humidification component 1402, the humidification component 1402 and the gas delivery device 1436 configured for determining, based on the humidification target value information, target operational information of a system associated with the patient, the system including the apparatus.

In one embodiment, an apparatus includes: a humidification component 1402 configured for holding a water volume 404, the humidification component 1402 comprised entirely of a non-metallic material, the non-metallic material configured for conducting heat to the water volume 404, the heat being received from a heating element 110; a respiratory gas conduit 810 including an input end 806 and an output end 804, the respiratory gas conduit 810 configured for receiving gas at the input end 806 and configured to transport the gas to the output end 804; and a heater wire 802 disposed inside the respiratory gas conduit 810, the heater wire 802 including: a sheathing; and at least one groove 904 disposed on the sheathing, the at least one groove 904 configured for wicking up water from a region of condensation within the respiratory gas conduit 810 and transporting wicked up water to a re-evaporation region.

In one embodiment, an apparatus includes: a humidification component 1402 configured for holding a water volume 404 and for adding water vapor to a gas to be provided to a patient to support breathing, the humidification component 1402 comprised entirely of a non-metallic material, the non-metallic material configured for conducting heat to the water volume 404, the heat being received from a heating element 110; a humidification component controller 1414 coupled with the humidification component 1402 and configured for receiving the humidification target value information 1410, the humidification component controller 1414 including: a humidification target value determiner 1416 configured for determining, based on received humidification target value information 1410, a humidification target value 1418 of at least two possible humidification target values, the humidification target value 1418 identifying a humidification level setting 1420 corresponding to the patient; a respiratory gas conduit 810 including an input end 806 and an output end 804, the respiratory gas conduit 810 configured for receiving gas at the input end 806 and configured to transport the gas to the output end 804; and a heater wire 802 disposed inside the respiratory gas conduit 810, the heater wire 802 including: a sheathing; and at least one groove 904 disposed on the sheathing, the at least one groove 904 configured for wicking up water from a region of condensation within the respiratory gas conduit 810 and transporting wicked up water to a re-evaporation region.

In one embodiment, an apparatus includes: a humidification component 1402 configured for holding a water volume 404 and for adding water vapor to a gas to be provided to a patient to support breathing, the humidification component 1402 comprised entirely of a non-metallic material, the non-metallic material configured for conducting heat to the water volume 404, the heat being received from a heating element 110; a respiratory gas conduit 810 including an input end 806 and an output end 804, the respiratory gas conduit 810 configured for receiving gas at the input end 806 and configured to transport the gas to the output end 804; a heater wire 802 disposed inside the respiratory gas conduit 810, the heater wire 802 including: a sheathing; and at least one groove 904 disposed on the sheathing, the at least one groove 904 configured for wicking up water from a region of condensation within the respiratory gas conduit 810 and transporting wicked up water to a re-evaporation region; a gas delivery device 1436 coupled with the humidification component 1402, the gas delivery device 1436 configured for controlling a delivery of the gas to the humidification component 1402; and a communication module 1434 coupled with the gas delivery device 1436 and the humidification component 1402, the communication module 1434 configured for communicating the humidification target value information 1410 between the gas delivery device controller 1442 and the humidification component 1402, the humidification component 1402 and the gas delivery device 1436 configured for determining, based on the humidification target value information, target operational information of a system associated with the patient, the system including the apparatus.

In one embodiment, a system for providing humidification to gas to be provided to a patient to support breathing includes: a humidification component 1402 configured for holding a water volume 404 and for adding water vapor to the gas; and a humidification component controller 1414 coupled with the humidification component 1402 and configured for receiving the humidification target value information 1410, the humidification component controller 1414 including: a humidification target value determiner 1416 configured for determining, based on received humidification target value information 1410, a humidification target value 1418 of at least two possible humidification target values, the humidification target value 1418 identifying a humidification level setting 1420 corresponding to the patient; a respiratory gas conduit 810 including an input end 806 and an output end 804, the respiratory gas conduit 810 configured for receiving gas at the input end 806 and configured to transport the gas to the output end 804; and a heater wire 802 disposed inside the respiratory gas conduit 810, the heater wire 802 including: a sheathing; and at least one groove 904 disposed on the sheathing, the at least one groove 904 configured for wicking up water from a region of condensation within the respiratory gas conduit 810 and transporting wicked up water to a re-evaporation region.

In one embodiment, a breathing circuit includes: respiratory gas conduit 810 including an input end 806 and an output end 804, the respiratory gas conduit 810 configured for receiving gas at the input end 806 and configured to transport the gas to the output end 804; a heater wire 802 disposed inside the respiratory gas conduit 810, the heater wire 802 including: a sheathing; and at least one groove 904 disposed on the sheathing, the at least one groove 904 configured for wicking up water from a region of condensation within the respiratory gas conduit 810 and transporting wicked up water to a re-evaporation region; a humidification component 1402 configured for holding a water volume 404 and for adding water vapor to a gas to be provided to a patient to support breathing; a gas delivery device 1436 coupled with the humidification component 1402, the gas delivery device 1436 configured for controlling a delivery of the gas to the humidification component 1402; and a communication module 1434 coupled with the gas delivery device 1436 and the humidification component 1402, the communication module 1434 configured for communicating the humidification target value information 1410 between the gas delivery device controller 1442 and the humidification component 1402, the humidification component 1402 and the gas delivery device 1436 configured for determining, based on the humidification target value information, target operational information of a system associated with the patient, the system including the breathing circuit.

In one embodiment, a method for humidifying respiratory gases, the method including: receiving 202 electrical energy at a heating element 110; converting 204, by the heating element 110, the electrical energy to electromagnetic radiation, wherein the electromagnetic radiation is transferred to a water volume 404 of a humidification component 1402, thereby heating the water volume 404 to achieve a heated water volume 404 that produces water vapor; flowing 206 respiratory gases across the heated water volume 404, wherein the water vapor humidifies the respiratory gases; sensing 502, by at least one sensor 410, water related information in the humidification component 1402, the at least one sensor 410 positioned external to the humidification component 1402 and coupled with a control module 420; and providing 504, by the at least one sensor 410, the water related information to the control module 420, the water related information including data configured for being used to control an operation of a water level control element.

In one embodiment, a method for humidifying respiratory gases includes: receiving 202 electrical energy at a heating element 110; converting 204, by the heating element 110, the electrical energy to electromagnetic radiation, wherein the electromagnetic radiation is transferred to a water volume 404 of a humidification component 1402, thereby heating the water volume 404 to achieve a heated water volume 404 that produces water vapor; and flowing 206 respiratory gases across the heated water volume 404, wherein the water vapor humidifies the respiratory gases, wherein the humidification component 1402 is entirely comprised of a non-metallic material.

In one embodiment, a method for humidifying respiratory gases includes: receiving 202 electrical energy at a heating element 110; converting 204, by the heating element 110, the electrical energy to electromagnetic radiation, wherein the electromagnetic radiation is transferred to a water volume 404 of a humidification component 1402, thereby heating the water volume 404 to achieve a heated water volume 404 that produces water vapor; flowing 206 respiratory gases across the heated water volume 404, wherein the water vapor humidifies the respiratory gases; sensing 502, by at least one sensor 410, water related information in the humidification component 1402, the at least one sensor 410 positioned external to the humidification component 1402 and coupled with a control module 420; and providing 504, by the at least one sensor 410, the water related information to the control module 420, the water related information including data configured for being used to control an operation of a water level control element, wherein the humidification component 1402 is entirely comprised of a non-metallic material.

A method for maintaining a water level in a humidification component, said method including: receiving 1302, at a humidification component 1402, heat from a heat source, the humidification component 1402 configured for holding a water volume, wherein the humidification component 1402 is entirely comprised of a non-metallic material; conducting 1304, by said non-metallic material, received heat through said humidification component into said water volume; sensing 502, by at least one sensor 410, water related information in said humidification component 1402, the at least one sensor 410 positioned external to said humidification component 1402 and coupled with a control module 420; and providing 504, by the at least one sensor 410, the water related information to the control module 420, the water related information including data configured for being used to control an operation of a water level control element.

In one embodiment, a method of manufacturing a device for humidifying respiratory gases includes: providing 302 a humidification component 1402 configured for holding a water volume 404; disposing 304 a heating element 110 within a base unit; and coupling 306 the humidification component 1402 with the base unit, wherein the heating element 110 is configured for receiving electrical energy and converting the electrical energy to electromagnetic radiation such that the electromagnetic radiation is transferred to the water volume 404, thereby heating the water volume 404 to achieve a heated water volume 404, and wherein the heating element 110 is independent of the humidification component 1402.

In one embodiment, a method of manufacturing a device for humidifying respiratory gases includes: providing 302 a humidification component 1402 configured for holding a water volume 404; disposing 304 a heating element 110 within a base unit; coupling 306 the humidification component 1402 with the base unit, wherein the heating element 110 is configured for receiving electrical energy and converting the electrical energy to electromagnetic radiation such that the electromagnetic radiation is transferred to the water volume 404, thereby heating the water volume 404 to achieve a heated water volume 404, and wherein the heating element 110 is independent of the humidification component 1402; and coupling 604 at least one sensor 410 with a control module 420, the at least one sensor 410 configured for sensing water related information in the humidification component 1402 and providing the water related information to the control module 420, the water related information including data configured for being used by the control module 420 to control an operation of a water level control element, wherein the at least one sensor 410 is positioned external to the humidification component 1402.

In one embodiment, a method of manufacturing a device for humidifying respiratory gases includes: providing 302 a humidification component 1402 configured for holding a water volume 404; disposing 304 a heating element 110 within a base unit; coupling 306 the humidification component 1402 with the base unit, wherein the heating element 110 is configured for receiving electrical energy and converting the electrical energy to electromagnetic radiation such that the electromagnetic radiation is transferred to the water volume 404, thereby heating the water volume 404 to achieve a heated water volume 404, and wherein the heating element 110 is independent of the humidification component 1402; providing 1102 a heater wire 802, the heater wire 802 configured for heating gas inside and between an input and output end 804 of a respiratory gas conduit 810; disposing 1104 a sheathing on a wire component of the heater wire 802, wherein the sheathing includes a hydrophilic component; and disposing 1106 at least one groove 904 on the sheathing, the at least one groove 904 configured for wicking up water from a region of condensation and transporting wicked up water to a re-evaporation region.

In one embodiment, a method of manufacturing a device for humidifying respiratory gases includes: providing 302 a humidification component 1402 configured for holding a water volume 404; disposing 304 a heating element 110 within a base unit; coupling 306 the humidification component 1402 with the base unit, wherein the heating element 110 is configured for receiving electrical energy and converting the electrical energy to electromagnetic radiation such that the electromagnetic radiation is transferred to the water volume 404, thereby heating the water volume 404 to achieve a heated water volume 404, and wherein the heating element 110 is independent of the humidification component 1402; coupling 604 at least one sensor 410 with a control module 420, the at least one sensor 410 configured for sensing water related information in the humidification component 1402 and providing the water related information to the control module 420, the water related information including data configured for being used by the control module 420 to control an operation of a water level control element, wherein the at least one sensor 410 is positioned external to the humidification component 1402; providing 1102 a heater wire 802, the heater wire 802 configured for heating gas inside and between an input and output end 804 of a respiratory gas conduit 810; disposing 1104 a sheathing on a wire component of the heater wire 802, wherein the sheathing includes a hydrophilic component; and disposing 1106 at least one groove 904 on the sheathing, the at least one groove 904 configured for wicking up water from a region of condensation and transporting wicked up water to a re-evaporation region.

In one embodiment, a method of manufacturing a device for humidifying respiratory gases includes: providing 302 a humidification component 1402 configured for holding a water volume 404; disposing 304 a heating element 110 within a base unit; coupling 306 the humidification component 1402 with the base unit, wherein the heating element 110 is configured for receiving electrical energy and converting the electrical energy to electromagnetic radiation such that the electromagnetic radiation is transferred to the water volume 404, thereby heating the water volume 404 to achieve a heated water volume 404, and wherein the heating element 110 is independent of the humidification component 1402; providing 1102 a heater wire 802, the heater wire 802 configured for heating gas inside and between an input and output end 804 of a respiratory gas conduit 810; disposing 1104 a sheathing on a wire component of the heater wire 802, wherein the sheathing includes a hydrophilic component; and disposing 1106 at least one groove 904 on the sheathing, the at least one groove 904 configured for wicking up water from a region of condensation and transporting wicked up water to a re-evaporation region.

All statements herein reciting principles, aspects, and embodiments of the technology as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present technology, therefore, is not intended to be limited to the embodiments shown and described herein. Rather, the scope and spirit of present technology is embodied by the appended claims.

What is claimed is:

1. A respiratory gas conduit comprising:
   a heater wire comprising:
      a wire component,
      a groove that extends along a length of the heater wire; and
      a plurality of threads, each having a first end attached to an outer surface of the heater wire that faces away from the wire component and a second, opposite, free end extending away from the heater wire, the plurality of threads braided around the outer geometry of the heater wire.

2. The respiratory gas conduit of claim 1, wherein the braided threads comprise braided fibers having spaces between the fibers with a geometry configured to facilitate capillary action.

3. The respiratory gas conduit of claim 2, wherein the spaces form a plurality of channels for facilitating a movement of a liquid through the braided threads along the length of the heater wire.

4. The respiratory gas conduit of claim 3, wherein the heater wire comprises a first portion and a second portion, wherein the second portion is configured to be hotter than the first portion.

5. The respiratory gas conduit of claim 4, wherein the plurality of channels are configured to assist in movement of the liquid from the first portion to the second hotter portion of the heater wire for re-evaporation of the liquid.

6. The respiratory gas conduit of claim 5, further comprising a condensation region and a re-evaporation region, wherein the first portion of the heater wire is disposed in the condensation region, and wherein the second portion of the heater wire is disposed in the re-evaporation region.

7. The respiratory gas conduit of claim 6, wherein the groove is configured to:
   wick water that has condensed in the condensation region into a portion of the groove in the condensation region; and
   transport the wicked water within the groove along a length of the heater wire away from the portion of the groove in the condensation region to the re-evaporation region.

8. A respiratory gas conduit comprising:
   a heater wire comprising:
      a wire component,
      a groove that extends along a length of the heater wire; and
      a plurality of threads, each having a first end attached to an outer surface of the heater wire that faces away from the wire component and a second, opposite, free end that extends away from the heater wire.

9. The respiratory gas conduit of claim 8, wherein threads comprise fibers having spaces between the fibers with a geometry configured to facilitate capillary action.

10. The respiratory gas conduit of claim 9, wherein the spaces form a plurality of channels for facilitating a movement of a liquid through the threads along the length of the heater wire.

11. The respiratory gas conduit of claim 10, wherein the heater wire comprises a first portion and a second portion, wherein the second portion is configured to be hotter than the first portion.

12. The respiratory gas conduit of claim 11, wherein the plurality of channels are configured to assist in movement of the liquid from the first portion to the second hotter portion of the heater wire for re-evaporation of the liquid.

13. The respiratory gas conduit of claim 12, further comprising a condensation region and a re-evaporation region, wherein the first portion of the heater wire is disposed in the condensation region, and wherein the second portion of the heater wire is disposed in the re-evaporation region.

14. The respiratory gas conduit of claim 13, wherein the groove is configured to:
wick water that has condensed in the condensation region into a portion of the groove in the condensation region; and
transport the wicked water along a length of the groove away from the portion of the groove in the condensation region to the re-evaporation region.

15. A method, comprising:
wicking liquid from a region of condensation within a respiratory gas conduit, said wicking liquid performed by at least one groove and at least one extending fiber disposed on a heater wire, wherein said heater wire is positioned within a respiratory gas conduit, wherein said at least one extending fiber comprises a woven or braided portion and a plurality of channels positioned within said woven or braided portion, said plurality of channels being configured for facilitating a movement of a liquid in a direction generally aligned with said heater wire; and
transporting, by said at least one groove and said plurality of channels, the wicked liquid from said region of condensation within said respiratory gas conduit to a re-evaporation region,
wherein the region of condensation is a portion of the respiratory gas conduit at which water accumulates and does not evaporate and wherein the at least one groove has a first width at an outer surface of the heater wire that is less than a second width of the at least one groove.

16. The method of claim 15, further comprising:
evaporating said transported wicked liquid by a hot surface of said heater wire in said re-evaporation region.

17. The method of claim 16, further comprising:
heating a first portion of a surface of the heater wire that is located in the region of condensation to a first temperature; and
heating a second portion of a surface of the heater wire that is located in the re-evaporation region to a second temperature that is higher than the first temperature to form the hot surface.

18. The method of claim 17, wherein transporting by said at least one groove and said plurality of channels comprises drawing wicked water that is in the groove, through capillary action, towards an unwetted part of the groove.

19. The method of claim 15, further comprising transporting additional liquid along a plurality of additional grooves equally spaced on the heater wire.

* * * * *